US009139552B2

(12) United States Patent
Xiao et al.

(10) Patent No.: US 9,139,552 B2
(45) Date of Patent: Sep. 22, 2015

(54) INDENO-FUSED NAPHTHOPYRANS HAVING ETHYLENICALLY UNSATURATED GROUPS

(75) Inventors: Wenjing Xiao, Murrysville, PA (US); Barry Van Gemert, Delmont, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 13/326,546

(22) Filed: Dec. 15, 2011

(65) Prior Publication Data

US 2012/0132870 A1     May 31, 2012

Related U.S. Application Data

(60) Continuation-in-part of application No. 12/873,735, filed on Sep. 1, 2010, now Pat. No. 8,147,725, which is a continuation-in-part of application No. 12/136,339, filed on Jun. 10, 2008, now abandoned, which is a division of application No. 11/102,279, filed on Apr. 8, 2005, now abandoned.

(51) Int. Cl.

| | |
|---|---|
| *G02B 5/23* | (2006.01) |
| *C07D 311/92* | (2006.01) |
| *C07D 311/78* | (2006.01) |
| *C07D 405/04* | (2006.01) |
| *C07D 407/12* | (2006.01) |
| *C07D 409/04* | (2006.01) |
| *C07D 493/04* | (2006.01) |
| *C07D 495/04* | (2006.01) |
| *C09K 9/02* | (2006.01) |
| *G03C 1/73* | (2006.01) |
| *G02C 7/02* | (2006.01) |
| *G02F 1/03* | (2006.01) |
| *G02F 1/07* | (2006.01) |
| *G03C 1/685* | (2006.01) |

(52) U.S. Cl.
CPC ............ *C07D 311/92* (2013.01); *C07D 311/78* (2013.01); *C07D 405/04* (2013.01); *C07D 407/12* (2013.01); *C07D 409/04* (2013.01); *C07D 493/04* (2013.01); *C07D 495/04* (2013.01); *C09K 9/02* (2013.01); *G03C 1/73* (2013.01); *C09K 2211/1007* (2013.01); *C09K 2211/1022* (2013.01); *C09K 2211/1029* (2013.01); *C09K 2211/1044* (2013.01); *C09K 2211/1088* (2013.01); *G02B 5/23* (2013.01); *G03C 1/685* (2013.01)

(58) Field of Classification Search
USPC .......... 252/586, 582; 544/130, 363, 364, 375, 544/150, 333; 546/196; 549/382; 448/311.4; 351/159.01; 359/241
See application file for complete search history.

(56) References Cited

U.S. PATENT DOCUMENTS

| | | |
|---|---|---|
| 3,933,509 A | 1/1976 | Noguchi et al. |
| 4,929,693 A | 5/1990 | Akashi et al. |
| 4,931,220 A | 6/1990 | Haynes et al. |
| 5,066,818 A | 11/1991 | Gemert et al. |
| 5,166,345 A | 11/1992 | Akashi et al. |
| 5,236,958 A | 8/1993 | Miyashita |
| 5,238,981 A | 8/1993 | Knowles |
| 5,252,742 A | 10/1993 | Miyashita |
| 5,274,132 A | 12/1993 | VanGemert |
| 5,359,085 A | 10/1994 | Iwamoto et al. |
| 5,458,814 A | 10/1995 | Kumar et al. |
| 5,578,252 A | 11/1996 | Van Gemert et al. |
| 5,645,767 A | 7/1997 | Van Gemert |
| 5,645,768 A | 7/1997 | Melzig et al. |
| 5,650,098 A | 7/1997 | Kumar et al. |
| 5,651,923 A | 7/1997 | Kumar et al. |
| 5,658,501 A | 8/1997 | Kumar et al. |
| 5,698,141 A | 12/1997 | Kumar |
| 5,707,557 A | 1/1998 | Melzig et al. |
| 5,723,072 A | 3/1998 | Kumar |
| 5,753,146 A | 5/1998 | Van Gemert et al. |
| 5,770,115 A | 6/1998 | Misura |
| 5,811,034 A | 9/1998 | Lin |
| 5,821,287 A | 10/1998 | Hu et al. |
| 5,952,515 A | 9/1999 | Melzig et al. |
| 5,955,520 A | 9/1999 | Heller et al. |
| 5,961,892 A | 10/1999 | Gemert et al. |
| 6,018,059 A | 1/2000 | Chan |
| 6,022,497 A | 2/2000 | Kumar |
| 6,025,026 A | 2/2000 | Smith et al. |

(Continued)

FOREIGN PATENT DOCUMENTS

| | | |
|---|---|---|
| EP | 0446717 A2 | 9/1991 |
| EP | 1038870 A1 | 9/2000 |

(Continued)

OTHER PUBLICATIONS

Araujo, R. J. et al., "Photochromism," Techniques in Chemistry, 1971, pp. 734-853, vol. III, Chapter 3, Glenn H. Brown, Editor, Wiley-Interscience a Division of John Wiley & Sons, Inc.

*Primary Examiner* — Bijan Ahvazi

(74) *Attorney, Agent, or Firm* — The Webb Law Firm

(57) ABSTRACT

The present invention relates to indeno-fused naphthopyrans, and in particular indeno[2',3':3,4]naphtho[1,2-b]pyrans having certain groups bonded to the 3, 6, 7, 11, and 13 positions thereof. The indeno-fused naphthopyrans of the present invention have an ethylenically unsaturated group selected from ($C_1$-$C_6$ alkyl)acrylate and ($C_1$-$C_6$ alkyl)acrylamide, that is linked to the 11 position or 13 position thereof. The present invention also relates to photochromic articles and photochromic compositions containing such indeno-fused naphthopyrans.

15 Claims, No Drawings

(56) References Cited

U.S. PATENT DOCUMENTS

| | | | |
|---|---|---|---|
| 6,036,890 A | 3/2000 | Melzig et al. | |
| 6,068,797 A | 5/2000 | Hunt | |
| 6,096,246 A | 8/2000 | Chan et al. | |
| 6,113,814 A | 9/2000 | Gemert et al. | |
| 6,146,554 A | 11/2000 | Melzig et al. | |
| 6,150,430 A | 11/2000 | Walters et al. | |
| 6,153,126 A | 11/2000 | Kumar | |
| 6,190,580 B1 | 2/2001 | Melzig et al. | |
| 6,225,466 B1 | 5/2001 | Mann et al. | |
| 6,296,785 B1 | 10/2001 | Nelson et al. | |
| 6,340,765 B1* | 1/2002 | Momoda et al. | 549/330 |
| 6,392,043 B1 | 5/2002 | Bourchteine et al. | |
| 6,398,987 B1 | 6/2002 | Breyne et al. | |
| 6,399,791 B1 | 6/2002 | Breyne et al. | |
| 6,469,076 B1* | 10/2002 | Momoda et al. | 524/86 |
| 6,506,322 B1 | 1/2003 | Breyne et al. | |
| 6,555,028 B2 | 4/2003 | Walters et al. | |
| 6,630,597 B1 | 10/2003 | Lin et al. | |
| 6,641,874 B2 | 11/2003 | Kuntz et al. | |
| 6,683,709 B2 | 1/2004 | Mann et al. | |
| 6,719,925 B1 | 4/2004 | Breyne et al. | |
| 6,723,859 B2 | 4/2004 | Kawabata et al. | |
| 6,747,145 B2 | 6/2004 | Zhao et al. | |
| 6,846,892 B2 | 1/2005 | Kindt-Larsen et al. | |
| 6,852,254 B2 | 2/2005 | Spaulding et al. | |
| 6,939,007 B2 | 9/2005 | Zhao et al. | |
| 6,963,003 B2 | 11/2005 | Qin | |
| 7,008,568 B2 | 3/2006 | Qin | |
| 7,074,943 B2 | 7/2006 | Qin | |
| 7,166,357 B2 | 1/2007 | Kumar et al. | |
| 7,247,262 B2 | 7/2007 | Evans et al. | |
| 7,256,246 B2 | 8/2007 | Kindt-Larsen et al. | |
| 7,262,295 B2 | 8/2007 | Walters et al. | |
| 7,320,826 B2 | 1/2008 | Kumar et al. | |
| 7,368,072 B2 | 5/2008 | Gemert et al. | |
| 7,527,754 B2 | 5/2009 | Chopra | |
| 7,556,750 B2 | 7/2009 | Xiao et al. | |
| 7,807,075 B2 | 10/2010 | Evans et al. | |
| 2001/0025948 A1* | 10/2001 | Walters et al. | 252/586 |
| 2001/0039356 A1 | 11/2001 | Chan et al. | |
| 2003/0000028 A1 | 1/2003 | Molock et al. | |
| 2003/0071247 A1 | 4/2003 | Petrovskaia et al. | |
| 2003/0141490 A1 | 7/2003 | Walters et al. | |
| 2003/0165686 A1 | 9/2003 | Blackburn et al. | |
| 2003/0180444 A1 | 9/2003 | Takekuma et al. | |
| 2003/0236376 A1 | 12/2003 | Kindt-Larsen et al. | |
| 2004/0185255 A1 | 9/2004 | Walters et al. | |
| 2004/0185268 A1 | 9/2004 | Kumar et al. | |
| 2004/0186241 A1 | 9/2004 | Gemert | |
| 2004/0191520 A1 | 9/2004 | Kumar et al. | |
| 2004/0197563 A1 | 10/2004 | Kye | |
| 2005/0004361 A1 | 1/2005 | Kumar et al. | |
| 2005/0175306 A1 | 8/2005 | Chong et al. | |
| 2005/0258408 A1 | 11/2005 | Molock et al. | |
| 2006/0022176 A1 | 2/2006 | Wang et al. | |
| 2006/0090848 A1 | 5/2006 | Koga et al. | |
| 2006/0100408 A1 | 5/2006 | Powell et al. | |
| 2006/0110520 A1 | 5/2006 | Midorikawa et al. | |
| 2006/0226400 A1 | 10/2006 | Xiao et al. | |
| 2006/0226401 A1 | 10/2006 | Xiao et al. | |
| 2006/0226402 A1 | 10/2006 | Kim et al. | |
| 2006/0227287 A1* | 10/2006 | Molock et al. | 351/163 |
| 2006/0228557 A1 | 10/2006 | Kim et al. | |
| 2007/0001155 A1 | 1/2007 | Walters et al. | |
| 2007/0249794 A1 | 10/2007 | Evans et al. | |
| 2008/0103301 A1 | 5/2008 | Chopra et al. | |
| 2009/0032782 A1 | 2/2009 | Kim et al. | |
| 2011/0042629 A1 | 2/2011 | Chopra et al. | |
| 2011/0108781 A1 | 5/2011 | Tomasulo | |
| 2011/0143141 A1 | 6/2011 | He et al. | |
| 2011/0190455 A1 | 8/2011 | Partington | |
| 2011/0248415 A1 | 10/2011 | Alvarez-Carrigan et al. | |
| 2011/0249235 A1 | 10/2011 | Duis et al. | |
| 2012/0145973 A1 | 6/2012 | Bancroft et al. | |
| 2012/0156508 A1 | 6/2012 | He et al. | |

FOREIGN PATENT DOCUMENTS

| | | |
|---|---|---|
| EP | 1054010 A1 | 11/2000 |
| EP | 1184379 A1 | 6/2002 |
| JP | 2000327676 A | 11/2000 |
| JP | 2004131593 A | 4/2004 |
| WO | 9737254 A1 | 10/1997 |
| WO | 9740409 A1 | 10/1997 |
| WO | 9748762 A1 | 12/1997 |
| WO | 9748993 A1 | 12/1997 |
| WO | 9828289 A1 | 7/1998 |
| WO | 9915518 A1 | 4/1999 |
| WO | 9923071 A1 | 5/1999 |
| WO | 00/05325 A1 | 2/2000 |
| WO | 0015630 A1 | 3/2000 |
| WO | 0119813 A1 | 3/2001 |
| WO | 0160811 A1 | 8/2001 |
| WO | 0170719 A2 | 9/2001 |
| WO | 0194336 A1 | 12/2001 |
| WO | 03056390 A2 | 7/2003 |
| WO | 2004041961 A1 | 5/2004 |
| WO | 2005/005570 A1 | 1/2005 |
| WO | 2005/105874 A1 | 11/2005 |
| WO | 2006022825 A1 | 3/2006 |
| WO | 2006/110219 A1 | 10/2006 |
| WO | 2006/110305 | 10/2006 |
| WO | 2006110520 A1 | 10/2006 |
| WO | 2010/020770 A1 | 2/2010 |
| WO | 2011/053615 A1 | 5/2011 |
| WO | 2011053615 A1 | 5/2011 |
| WO | 2011/130137 A2 | 10/2011 |
| WO | 2011/130139 A1 | 10/2011 |
| WO | 2012/082999 | 6/2012 |

* cited by examiner

INDENO-FUSED NAPHTHOPYRANS HAVING ETHYLENICALLY UNSATURATED GROUPS

CROSS REFERENCE TO RELATED APPLICATIONS

This application is a continuation-in-part of U.S. patent application Ser. No. 12/873,735, filed on Sep. 1, 2010, which is a continuation in part of U.S. patent application Ser. No. 12/136,339, filed on Jun. 10, 2008, now abandoned, which is a divisional of U.S. patent application Ser. No. 11/102,279, filed on Apr. 8, 2005, now abandoned, the disclosure of each of which is incorporated herein by reference in its entirety.

FIELD

The present invention relates indeno-fused naphthopyrans having an ethylenically unsaturated group selected from ($C_1$-$C_6$ alkyl)acrylate and ($C_1$-$C_6$ alkyl)acrylamide, that is linked to the 11 position or 13 position thereof, and to photochromic articles and photochromic compositions containing such indeno-fused naphthopyrans.

BACKGROUND

In response to certain wavelengths of electromagnetic radiation (or "actinic radiation"), photochromic compounds, such as indeno-fused naphthopyrans, typically undergo a transformation from one form or state to another form, with each form having a characteristic or distinguishable absorption spectrum associated therewith. Typically, upon exposure to actinic radiation, many photochromic compounds are transformed from a closed-form, which corresponds to an unactivated (or bleached, e.g., substantially colorless) state of the photochromic compound, to an open-form, which corresponds to an activated (or colored) state of the photochromic compound. In the absence of exposure to actinic radiation, such photochromic compounds are reversibly transformed from the activated (or colored) state, back to the unactivated (or bleached) state. Compositions and articles, such as eyewear lenses, that contain photochromic compounds or have photochromic compounds applied thereto (e.g., in form of a photochromic coating composition) typically display colorless (e.g., clear) and colored states that correspond to the colorless and colored states of the photochromic compounds contained therein or applied thereto.

Photochromic compounds can be incorporated into a polymeric matrix, which can result in the formation of a photochromic article, such as a photochromic ophthalmic lens, including, but not limited to photochromic contact lenses. With photochromic contact lenses, for example, it is typically desirable that the photochromic compound undergoes minimal to no migration out of the contact lens matrix, such as into a cleaning solution and/or a human eye. Additionally, in some applications it is desirable that the photochromic compound undergo minimal to no migration within the contact lens matrix, such as from a central or pupil area of the lens out into the surrounding matrix area thereof.

It would be desirable to develop new indeno-fused naphthopyran compounds that are photochromic, and which undergo minimal to no migration within and/or out of a polymeric matrix into which they are incorporated. Additionally, it would be desirable that such newly developed indeno-fused naphthopyran compounds possess photochromic properties, such as but not limited to, fade rate and/or optical density properties, that are at least the same as those of conventional indeno-fused naphthopyran compounds.

SUMMARY

In accordance with some embodiments of the present invention, there is provided an indeno-fused naphthopyran represented by the following Formula (I),

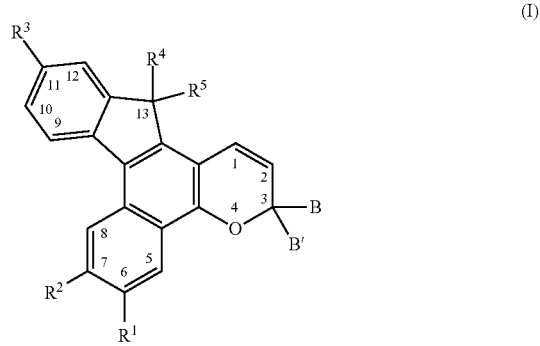

The $R^1$ group of Formula (I), which is at Position-6 of Formula (I), is $R_6O$—, wherein $R_6$ is selected from linear or branched $C_1$-$C_{20}$ alkyl, $C_3$-$C_{12}$ cycloalkyl, and $C_3$-$C_{12}$ heterocycloalkyl.

The $R^2$ group of Formula (I), which is at Position-7 of Formula (I), is, with some embodiments, —N($R_{11}'$)$R_{12}'$, wherein $R_{11}'$ and $R_{12}'$ are each independently hydrogen, $C_1$-$C_8$ alkyl, $C_3$-$C_{20}$ cycloalkyl, or $C_1$-$C_{20}$ alkoxyalkyl, or $R_{11}'$ and $R_{12}'$ come together with the nitrogen atom to form a bridged ring $C_4$-$C_{20}$ hetero-bicycloalkyl, and a fused ring $C_3$-$C_{20}$ hetero-polycyclic alkyl ring.

With some further embodiments, the $R^2$ group of Formula (I) is a nitrogen containing ring substituent represented by the following Formula (IIIA):

With reference to Formula (IIIA), each —Y— is independently chosen for each occurrence from —$CH_2$—, —CH($R_{13}'$)—, —C($R_{13}'$)$_2$—, and Z is —Y—, —O—, —S—, —S(O)—, —$SO_2$—, —NH—, —N($R_{13}'$)—, wherein each $R_{13}'$ is independently $C_1$-$C_6$ alkyl, m is an integer 1, 2 or 3, and p is an integer 0, 1, 2, or 3, provided that when p is 0, Z is —Y—.

The $R^3$ group of Formula (I), which is at Position-11 of Formula (I) can be selected from: hydrogen; linear or branched $C_1$-$C_{20}$ alkyl; or optionally substituted aryl. The optional aryl substituents are selected from: hydroxyl; halo; carbonyl; $C_1$-$C_6$ alkoxycarbonyl; cyano; halo($C_1$-$C_6$)alkyl; $C_1$-$C_6$ alkyl; $C_1$-$C_6$ alkoxy; —N($R_{11}'$)$R_{12}'$ in which $R_{11}'$ and $R_{12}'$ are each as described above; the nitrogen containing ring substituent represented by Formula (IIIA) wherein Formula (IIIA) is as described above; and optionally substituted aryl (in which the optional substituents are selected from: hydroxyl; halo; carbonyl; $C_1$-$C_6$ alkoxycarbonyl; cyano; halo ($C_1$-$C_6$)alkyl; $C_1$-$C_6$ alkyl; and $C_1$-$C_6$ alkoxy).

With further reference to Formula (I), $R^4$ and $R^5$ are each independently selected from linear or branched $C_1$-$C_{20}$ alkyl, and $C_3$-$C_{12}$ cycloalkyl. Alternatively, and with some embodiments, $R^4$ and $R^5$ together form an optionally substituted spirocycloalkyl group having from 3 to 10 carbon atoms in the spirocycloalkyl group inclusive of the spirocenter. The optional substituents of the spirocycloalkyl group are, with some embodiments, selected from linear or branched $C_1$-$C_{20}$ alkyl.

With additional reference to Formula (I), B and B' are each independently selected from an aryl group that is mono-substituted with a reactive substituent or a compatiblizing substituent; an unsubstituted aryl group; and a mono-, di-, tri- or tetra-substituted aryl group.

The substituents of the mono-, di-, tri- or tetra-substituted aryl groups from which B and B' can each be independently selected, are with some embodiments, independently selected from hydroxy, halo, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, linear or branched $C_1$-$C_{12}$ alkyl, linear or branched $C_1$-$C_{12}$ haloalkyl, linear or branched $C_1$-$C_{12}$ alkoxy, mono($C_1$-$C_{12}$)alkoxy($C_1$-$C_{12}$)alkyl, acryloxy, methacryloxy, halogen, or —C(=O)$R^{21}$ wherein $R^{21}$ is —O$R^{22}$, —N($R^{23}$)$R^{24}$, wherein $R^{22}$ is allyl, $C_1$-$C_6$ alkyl, $C_1$-$C_6$ alkoxy($C_2$-$C_4$) alkyl or $C_1$-$C_6$ haloalkyl, and $R^{23}$ and $R^{24}$ are each independently $C_1$-$C_6$ alkyl, or $C_5$-$C_7$ cycloalkyl.

With further reference to Formula (I), B and B' can, with some embodiments, each independently selected from an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, in which the optional substituents thereof are $C_1$-$C_{12}$ alkyl or $C_1$-$C_{12}$ alkoxy.

With additional reference to Formula (I), B and B' can each independently be a mono-substituted phenyl, in which the mono-substituted phenyl has a substituent located at the para position thereof. The substituent is: a dicarboxylic acid residue; or derivative thereof; a diamine residue or derivative thereof; an amino alcohol residue or derivative thereof; a polyol residue or derivative thereof; —(CH$_2$)—, —(CH$_2$)$_t$— or —[O—(CH$_2$)$_t$]$_k$—, in which t ranges form 2 to 6 and k ranges from 1 to 50, and in which the substituent is connected to an aryl group on another photochromic material.

With further additional reference to Formula (I), $R^4$ and $R^5$ each are not selected from hydroxyl and $R_7$O—, where $R_7$ is selected from optionally substituted alkyl, optionally substituted cycloalkyl, optionally substituted heterocycloalkyl, optionally substituted aryl, and optionally substituted heteroaryl.

With still further reference to Formula (I), one of $R^2$, B, and B' is substituted with a group represented by the following Formula (VI),

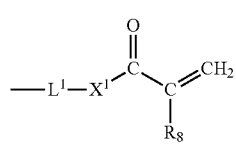

(VI)

With reference to Formula (VI), $R_8$ is selected from hydrogen and linear or branched $C_1$-$C_6$ alkyl, $X^1$ is selected from O and NH, and $L^1$ is a divalent hydrocarbyl group optionally interrupted with at least one of —C(O)—, —C(O)O—, —C(O)NH—, —NH—, —O—, and combinations of two or more thereof.

DESCRIPTION

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

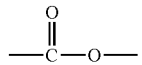

or equivalently —C(O)O—, is inclusive of the right-to-left representation thereof,

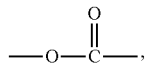

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used and referred to herein, the ideno-fused naphthopyrans represented by Formula (I) optionally further include one or more coproducts, resulting from the synthesis of such ideno-fused naphthopyrans.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic" and related terms, such as "photochromic compound," "photochromic indeno-naphthopyrans" and "photochromic indeno-naphthopyran compounds" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound, such as an indeno-fused naphthopyran.

As used herein, the term "photochromic compound" and related terms, such as "photochromic indeno-fused naphthopyrans" and "photochromic indeno-fused napthopyran compounds" includes thermally reversible photochromic compounds and non-thermally reversible photochromic compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "ophthalmic substrate" means lenses, partially formed lenses, and lens blanks.

As used herein the term "display" means the visible or machine-readable representation of information in words, numbers, symbols, designs or drawings. Non-limiting examples of display articles, elements and devices include screens, monitors, and security elements, such as security marks.

As used herein the term "window" means an aperture adapted to permit the transmission of radiation therethrough. Non-limiting examples of windows include automotive and aircraft transparencies, filters, shutters, and optical switches.

As used herein the term "mirror" means a surface that specularly reflects a large or substantial fraction of incident light.

As used herein the term "liquid crystal cell" refers to a structure containing a liquid crystal material that is capable of being ordered. Active liquid crystal cells are cells in which the liquid crystal material is capable of being reversibly and controllably switched or converted between ordered and disordered states, or between two ordered states by the application of an external force, such as electric or magnetic fields. Passive liquid crystal cells are cells in which the liquid crystal material maintains an ordered state. A non-limiting example of an active liquid crystal cell element or device is a liquid crystal display.

As used herein the term "coating" means a supported film derived from a flowable composition, which can or can not have a uniform thickness, and specifically excludes polymeric sheets. A layer that includes one or more photochromic compounds of the present invention can, with some embodiments, be a photochromic coating.

As used herein the term "sheet" means a pre-formed film having a generally uniform thickness and capable of self-support.

As used herein the term "connected to" means in direct contact with an object or indirect contact with an object through one or more other structures or materials, at least one of which is in direct contact with the object. For purposes of non-limiting illustration, a coating containing one or more photochromic compounds of the present invention, for example, can be in direct contact (e.g., abutting contact) with at least a portion of a substrate, such as an optical article, or it can be in indirect contact with at least a portion of the substrate through one or more other interposed structures or materials, such as a monomolecular layer of a coupling or adhesive agent. For example, although not limiting herein, a coating containing one or more photochromic compounds of the present invention, can be in contact with one or more other interposed coatings, polymer sheets or combinations thereof, at least one of which is in direct contact with at least a portion of the substrate.

As used herein, the term "photosensitive material" means materials that physically or chemically respond to electromagnetic radiation, including, but not limited to, phosphorescent materials and fluorescent materials.

As used herein, the term "non-photosensitive materials" means materials that do not physically or chemically respond to electromagnetic radiation, including, but not limited to, static dyes.

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "($C_1$-$C_6$ alkyl)acrylate" and similar terms, such as "($C_1$-$C_6$)acrylic acid ester" means $C_1$-$C_6$ alkylacrylates and/or acrylates. As used herein, the term "($C_1$-$C_6$)acrylic acid" means $C_1$-$C_6$ alkylacrylic acid and/or acrylic acid. Correspondingly, as used herein, the term "(meth)acrylate" and similar terms, such as "(meth)acrylic acid ester"

means methacrylates and/or acrylates. Further correspondingly, as used herein, the term "(meth)acrylic acid" means methacrylic acid and/or acrylic acid.

Other than in the operating examples, or where otherwise indicated, all numbers expressing quantities of ingredients, reaction conditions, and so forth used in the specification and claims are to be under stood as modified in all instances by the term "about."

As used herein, spatial or directional terms, such as "left", "right", "inner", "outer", "above", "below", and the like, relate to the invention as it is depicted in the drawing figures. However, it is to be understood that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, and unless otherwise indicated, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including fused-ring polycyclic aryl; heteroaryl, including fused-ring polycyclic heteroaryl; and aralkyl groups), and amine groups, such as —N($R^{11}$)($R^{12}$) where $R^{11}$ and $R^{12}$ are each independently selected from hydrogen, linear or branched $C_1$-$C_{20}$ alkyl, $C_3$-$C_{12}$ cycloakyl, $C_3$-$C_{12}$ heterocycloalkyl, aryl, and heteroaryl.

As used herein, the term "alkyl" means linear or branched $C_1$-$C_{20}$ alkyl, such as, but not limited to linear or branched $C_1$-$C_{10}$ alkyl or linear or branched $C_2$-$C_{10}$ alkyl. Examples of alkyl groups from which the various alkyl groups of the present invention can be selected from, include, but are not limited to, methyl, ethyl, propyl, isopropyl, butyl, isobutyl, sec-butyl, tert-butyl, pentyl, neopentyl, hexyl, heptyl, octyl, nonyl and decyl. Alkyl groups of the various compounds of the present invention can, with some embodiments, include one or more unsaturated linkages selected from —CH═CH— groups and/or one or more —C≡C— groups, provided the alkyl group is free of two or more conjugated unsaturated linkages. With some embodiments, the alkyl groups are free of unsaturated linkages, such as —CH═CH— groups and —C≡C— groups.

As used herein, the term "cycloalkyl" means groups that are appropriately cyclic, such as $C_3$-$C_{12}$ cycloalkyl (including, but not limited to, cyclic $C_5$-$C_7$ alkyl) groups. Examples of cycloalkyl groups include, but are not limited to, cyclopropyl, cyclobutyl, cyclopentyl, cyclohexyl, and cyclooctyl. The term "cycloalkyl" as used herein also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

As used herein, the term "heterocycloalkyl" means groups that are appropriately cyclic, such as $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

As used herein, the term "aryl" includes, but is not limited to, $C_5$-$C_{18}$ aryl, such as but not limited to, $C_5$-$C_{10}$ aryl (including fused ring polycyclic aryl groups). Examples of aryl groups include, but are not limited to, phenyl, naphthyl, and anthracenyl.

As used herein, the term "heteroaryl," includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, isoquinoline, and pyrimidinyl.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

As used herein, the term "aralkyl," includes but is not limited to $C_6$-$C_{24}$ aralkyl, such as but not limited to $C_6$-$C_{10}$ aralkyl, means an aryl group substituted with an alkyl group that is bonded (or linked) to another group. Examples of aralkyl groups include, but are not limited to, benzyl, and phenethyl.

As used herein the term "hydrocarbyl" and similar terms, such as "hydrocarbyl substituent," means: linear or branched $C_1$-$C_{20}$ alkyl (e.g., linear or branched $C_1$-$C_{10}$ alkyl); linear or branched $C_2$-$C_{20}$ alkenyl (e.g., linear or branched $C_2$-$C_{10}$ alkenyl); linear or branched $C_2$-$C_{20}$ alkynyl (e.g., linear or branched $C_2$-$C_{10}$ alkynyl); $C_3$-$C_{12}$ cycloalkyl (e.g., $C_3$-$C_{10}$ cycloalkyl); $C_5$-$C_{18}$ aryl (including polycyclic aryl groups) (e.g., $C_5$-$C_{10}$ aryl); and $C_6$-$C_{24}$ aralkyl (e.g., $C_6$-$C_{10}$ aralkyl). As used herein the term "hydrocarbyl" is inclusive of "heterohydrocarbyl," which is a hydrocarbyl in which at least one carbon, but less than all of the carbons thereof, has been replaced with a heteroatom, such as, but not limited to, O, N, S, and combinations thereof. Examples of heterohydrocarbyls from which a hydrocarbyl can be selected include, but are not limited to: $C_3$-$C_{12}$ heterocycloalkyl (having at least one hetero atom in the cyclic ring); and $C_5$-$C_{18}$ heteroaryl (having at least one hetero atom in the aromatic ring).

Representative alkyl groups, from which hydrocarbyl groups can be selected, include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups, from which hydrocarbyl groups can be selected, include but are not limited to vinyl, allyl and propenyl. Representative alkynyl groups include but are not limited to ethynyl, 1-propynyl, 2-propynyl, 1-butynyl, and 2-butynyl. Representative cycloalkyl groups, from which hydrocarbyl groups can be selected, include but are not limited to cyclopropyl, cyclobutyl, cyclopentyl, cyclohexyl, and cyclooctyl substituents. Representative heterocycloalkyl groups, from which hydrocarbyl groups can be selected, include but are not limited to tetrahydrofuranyl, tetrahydropyranyl and piperidinyl, including but not limited to piperindin-4-yl. Representative aryl groups, from which hydrocarbyl groups can be selected, include but are not limited to phenyl, naphthyl, anthracenyl, phenantrenyl and triptycenyl. Representative heteroaryl groups, from which hydrocarbyl groups can be selected, include but are not limited to furanyl, pyranyl and pyridinyl. Representative aralkyl groups, from which hydrocarbyl groups can be selected, include but are not limited to benzyl, and phenethyl.

The term "substituted hydrocarbyl" as used herein means a hydrocarbyl group in which at least one hydrogen thereof has been replaced or substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl; alkenyl; alkynyl; cycloalkyl; heterocycloalkyl, such as piperidinyl, including but not limited to piperidin-4-yl, optionally substituted with, for example, at least one linear or branched $C_1$-$C_{10}$ alkyl group; aryl, including hydroxyl substituted aryl, such as phenol, optionally substituted with, for example, at least one linear or branched $C_1$-$C_{10}$ alkyl group; heteroaryl; and aralkyl groups), and amine groups, such as —$N(R_{11}')(R_{12}')$ where $R_{11}'$ and $R_{12}'$ are each independently selected from hydrogen, hydrocarbyl and substituted hydrocarbyl.

For purposes of non-limiting illustration, the hydrocarbyl, of a substituted hydrocarbyl, can be selected from one or more of the hydrocarbyl groups described previously herein, such as a $C_3$-$C_{12}$ heterocycloalkyl group, such as piperidinyl, which can be substituted with one or more of the substituting groups described previously herein, such as one or more linear or branched $C_1$-$C_{25}$ alkyl groups. For purposes of further non-limiting illustration, the hydrocarbyl, of a substituted hydrocarbyl, can be selected from one or more of the hydrocarbyl groups described previously herein, such as an aryl group, such as phenyl, which can be substituted with one or more of the substituting groups described previously herein, such as one or more hydroxyl groups and/or one or more linear or branched $C_1$-$C_{25}$ alkyl groups.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can, with some embodiments, each be independently selected, can in each case be independently and optionally interrupted with at least one of —O—, —S—, —C(O)—, —C(O)O—, —OC(O)O—, —C(O)N($R^9$)—, —S(O)—, —$SO_2$—, —N($R^9$)— and —Si($R^9$)($R^{10}$)—. As used herein, by interrupted with at least one of —O—, —S—, —C(O)—, —C(O)O—, —OC(O)O—, —S(O)—, —$SO_2$—, —N($R^9$)—, and —Si($R^9$)($R^{10}$)—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two or more of the above recited linking groups, which can be adjacent to each other or separated by one or more carbons. For purposes of non-limiting illustration, a combination of adjacent —C(O)— and —N($R^9$)— can provide a divalent amide linking or interrupting group, —C(O)—N($R^9$)—. For purposes of further non-limiting illustration, a combination of adjacent —N($R^9$)—, —C(O)— and —O— can provide a divalent carbamate (or urethane) linking or interrupting group, —N($R^9$)—C(O)—O—, where $R^9$ is hydrogen. The $R^9$ and $R^{10}$ groups, of the previously recited interrupting groups, can each be independently selected from hydrocarbyl and heterohydrocarbyl groups, which can each be further independently selected from those classes and examples of hydrocarbyl and heterohydrocarbyl groups.

The indeno-fused naphthopyran compounds of the present invention can be referred to herein with regard to various groups at (or bonded to) various positions of the indeno-fused naphthopyran compounds. The positions are referred to herein with regard to the ring-positions as enumerated in Formula (I). With reference to Formula (I): $R^1$ is at the 6-position (or Position-6); $R^2$ is at the 7-position (or Position-7); $R^3$ is at the 11-position (or Position-11); $R^4$ and $R^5$ are each at the 13-position (or Position-13); and B and B' are each at the 3-position (or Position-3) of the indeno-fused naphthopyran represented by Formula (I).

The indeno-fused naphthopyrans represented by Formula (I) can be generally referred to herein as indeno[2',3':3,4]naphtho[1,2-b]pyrans or indeno[2',3':3,4]naphtho[1,2-b]pyran compounds, or as 3H-13H-indeno[2',3':3,4]naphtho[1,2-b]pyrans or 3H-13H-indeno[2',3':3,4]naphtho[1,2-b]pyran compounds.

As used herein, the term "divalent" with regard to divalent linking groups, such as but not limited to those described herein with reference to Formula (VI), means a group that has two covalent bonds that serve to link the linking group to two other groups, such as, but not limited to, the photochromic compound represented by Formula (I) and a separate group, such as, but not limited to the group represented by Formula (VI) or a portion thereof.

The indeno-fused naphthopyran compounds of the present invention, and compositions, materials and articles containing such indeno-fused naphthopyran compounds, are described in further detail as follows.

With further reference to Formula (I), $R^1$ can, with some embodiments, be selected from $R_6O$—, where $R_6$ is linear or branched $C_1$-$C_6$ alkyl. With some embodiments, $R^1$ of Formula (I) is selected from $R_6O$—, where $R_6$ is linear or branched $C_1$-$C_4$ alkyl.

The $R^2$ group of Formula (I), with some embodiments, is selected from: —$N(R_{11}')R_{12}'$, where $R_{11}'$ and $R_{12}'$ are each independently hydrogen, $C_1$-$C_8$ alkyl, or $R_{11}'$ and $R_{12}'$ come together with the nitrogen atom to form fused ring $C_5$-$C_{15}$ hetero-polycyclic alkyl; or the nitrogen containing ring substituent represented by Formula (IIIA), as described previously herein.

The $R^2$ group of Formula (I), with some further embodiments, is selected from, $N(R_{11}')R_{12}'$, where $R_{11}'$ and $R_{12}'$ are each independently hydrogen, and $C_1$-$C_8$ alkyl. Alternatively, the $R^2$ group of Formula (I), with some embodiments, is selected from, $N(R_{11}')R_{12}'$, where $R_{11}'$ and $R_{12}'$ come together with the nitrogen atom to form optionally substituted piperidino, optionally substituted octahydroisoquinoline or optionally substituted decahydroisoquinoline. Further alternatively, the $R^2$ group of Formula (I), with some embodiments, is selected from the nitrogen containing ring substituent represented by Formula (IIIA) as described previously herein, in which the nitrogen containing ring substituent represented by Formula (IIIA) is selected from optionally substituted morpholino. The optional substituents of the piperidino, octahydroisoquinoline, decahydroisoquinoline, and morpholino groups from which $R^2$ can be selected, with some embodiments, are each independently selected from linear or branched $C_1$-$C_{12}$ alkyl, linear or branched $C_1$-$C_{12}$ haloalky (including linear or branched $C_1$-$C_{12}$ perhaloalky), and linear or branched $C_1$-$C_{12}$ alkoxy.

The $R^3$ group of Formula (I), with some embodiments, is selected from hydrogen, linear or branched $C_1$-$C_{15}$ alkyl, and optionally substituted phenyl, the optional phenyl substituents being selected from halo, cyano, linear or branched halo ($C_1$-$C_6$)alkyl, linear or branched $C_1$-$C_6$ alkyl, and linear or branched $C_1$-$C_6$ alkoxy.

The $R^3$ group of Formula (I), with some further embodiments, is selected from hydrogen, linear or branched $C_1$-$C_{10}$ alkyl, and optionally substituted phenyl. The optional phenyl substituents are, with some embodiments, selected from halo, linear or branched halo($C_1$-$C_6$)alkyl, linear or branched $C_1$-$C_6$ alkyl, and linear or branched $C_1$-$C_6$ alkoxy.

With some embodiments, the $R^4$ and $R^5$ groups of Formula (I) are each independently selected from linear or branched $C_1$-$C_{20}$ alkyl.

With some further embodiments, the $R^4$ and $R^5$ groups of Formula (I) are each independently selected from linear or branched $C_1$-$C_{10}$ alkyl.

The B and B' groups of Formula (I), in accordance with some embodiments, are each independently optionally substituted phenyl. The optional substituents of the optionally substituted phenyl are, with some embodiments, selected from fluoro, linear or branched $C_1$-$C_{12}$ alkyl, linear or branched $C_1$-$C_{12}$ haloalkyl, linear or branched $C_1$-$C_{12}$ alkoxy, optionally substituted piperidino, optionally substituted morpholino, and optionally substituted piperazino. The optional substituents of the piperidino, morpholino and piperazino substituents, with some embodiments, are each independently selected from linear or branched $C_1$-$C_{12}$ alkyl, linear or branched $C_1$-$C_{12}$ haloalkyl, and linear or branched $C_1$-$C_{12}$ alkoxy.

The B and B' groups of Formula (I), in accordance with some further embodiments, are each independently optionally substituted phenyl. The optional substituents of the optionally substituted phenyl are, with some embodiments, selected from fluoro, $C_1$-$C_6$ alkyl, $C_1$-$C_6$ alkoxy, optionally substituted piperidino, optionally substituted piperazino and optionally substituted morpholino. The optional substituents of the piperidino, piperazino and morpholino substituents, with some embodiments, are each independently selected from linear or branched $C_1$-$C_6$ alkyl, linear or branched $C_1$-$C_6$ haloalkyl, and linear or branched $C_1$-$C_6$ alkoxy.

In accordance with some embodiments, and with reference to Formula (VI) of Formula (I), $L^1$ is selected from divalent linking groups represented by the following Formulas (VIIa) through (VIIe):

Formula (VIIa)

Formula (VIIb)

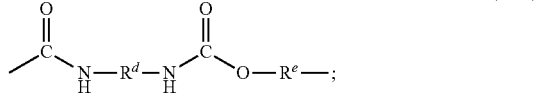
Formula (VIIc)

Formula (VIId)

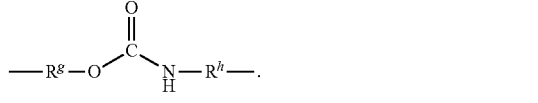
Formula (VIIe)

With reference to Formulas (VIIa) through (VIIe), $R^a$, $R^b$, $R^c$, $R^d$, $R^e$, $R^f$, $R^g$, and $R^h$ are each independently selected from divalent optionally substituted linear or branched $C_1$-$C_{10}$ alkyl, and divalent optionally substituted $C_3$-$C_{12}$ cycloalkyl. The optional substituents of the optionally substituted divalent linear or branched $C_1$-$C_{10}$ alkyl, and divalent $C_3$-$C_{12}$ cycloalkyl groups can be selected from include, but are not limited to, those classes and examples described previously herein. With some embodiments, The optional substituents of the optionally substituted divalent linear or branched $C_1$-$C_{10}$ alkyl, and optionally substituted divalent $C_3$-$C_{12}$ cycloalkyl groups are be selected from: linear or branched $C_1$-$C_{10}$ alkyl groups; $C_3$-$C_{12}$ cycloalkyl groups; $C_3$-$C_{12}$ heterocycloalkyl groups; halo groups, such as F, Cl, I, and Br; aryl groups, such as phenyl groups; and heteroaryl groups.

Examples of divalent linear or branched $C_1$-$C_{10}$ alkyl and divalent $C_3$-$C_{12}$ cycloalkyl groups from which $R^a$, $R^b$, $R^c$, $R^d$, $R^e$, $R^f$, $R^g$, and $R^h$ are each independently selected, include, but are not limited to, those examples as recited previously herein. For purposes of non-limiting illustration, and with some embodiments, examples of divalent linear or branched $C_1$-$C_{10}$ alkyl groups from which $R^a$, $R^b$, $R^c$, $R^d$, $R^e$, $R^f$, $R^g$, and $R^h$ are each independently selected include, but are not limited to, divalent methyl, divalent ethyl, divalent propyl, divalent butyl, divalent hexyl, divalent heptyl, divalent octyl, divalent nonyl, and divalent decyl, including in each case structural isomers of each thereof. For purposes of further non-limiting illustration, and with some embodiments, examples of divalent $C_3$-$C_{12}$ cycloalkyl groups from which $R^a$, $R^b$, $R^c$, $R^d$, $R^e$, $R^f$, $R^g$, and $R^h$ are each independently selected include, but are not limited to, divalent cyclopropyl, divalent cyclobutyl, divalent cyclopentyl, divalent cyclohexyl, 1,3,3-trimethyl-cyclohex-1,5-diyl, divalent cycloheptyl, divalent cyclooctyl, divalent cyclononyl, and divalent norbornyl.

With the indeno-fused naphthopyran compounds of the present invention one of $R^2$, B and B' is substituted with a group represented by Formula (VI) as described above. With some embodiments, $R^2$ is substituted with a group represented by Formula (VI), and more particularly $R^2$ is represented by the following Formula (VIIIa),

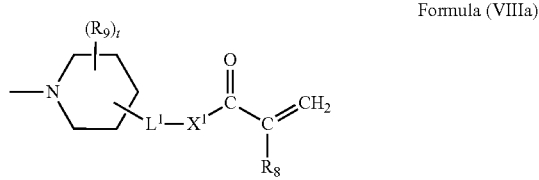

Formula (VIIIa)

With reference to Formula (VIIIa), t is 0 to 4, and $R_9$ independently for each t is selected from linear or branched $C_1$-$C_{10}$ alkyl, $C_3$-$C_{12}$ cycloalkyl, $C_3$-$C_{12}$ heterocycloalkyl, and aryl. The aryl groups from which $R_9$ can be selected include, but are not limited to, those classes and examples recited previously herein.

With the indeno-fused naphthopyran compounds of the present invention one of $R^2$, B and B' is substituted with a group represented by Formula (VI) as described above. With some embodiments, B or B' is substituted with a group represented by Formula (VI), and more particularly B or B' is represented by the following Formula (VIIb),

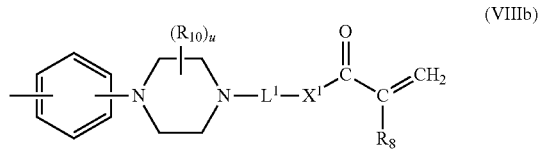

(VIIIb)

With reference to Formula (VIIb), u is 0 to 4, and $R_{10}$ independently for each u is linear or branched $C_1$-$C_{10}$ alkyl or $C_3$-$C_{12}$ cycloalkyl.

With further reference to Formula (VIIb), and with some embodiments, $L^1$ is selected from divalent linking groups represented by Formulas (VIIa), (VIIb), (VIIc), and (VIId) as described previously herein, where $R^a$, $R^b$, $R^c$, $R^d$, $R^e$, and $R^f$ are each independently selected from divalent linear or branched $C_1$-$C_{10}$ alkyl, and divalent $C_3$-$C_{12}$ cycloalkyl, and $R_{10}$ independently for each u is linear or branched $C_1$-$C_{10}$ alkyl. In accordance with some embodiments, when $L^1$ of Formula (VIIIb) is selected from divalent linking groups represented by Formulas (VIIa), (VIIb), (VIIc), and (VIId), $R_{10}$ independently for each u is linear or branched $C_1$-$C_6$ alkyl.

With further reference to Formula (VIIIa), and with some embodiments, $L^1$ is represented by Formula (VIIe) as described previously herein, where $R^g$, and $R^h$ are each independently selected from divalent linear or branched $C_1$-$C_{10}$ alkyl, and divalent $C_3$-$C_{12}$ cycloalkyl, and $R_9$ independently for each t is linear or branched $C_1$-$C_{10}$ alkyl. With some embodiments, when $L^1$ of Formula (VIIIa) is represented by Formula (VIIe), t is 0.

For purposes of non-limiting illustration, examples of indeno-fused naphthopyran compounds represented by Formula (I) include, but are not limited to, the following indeno-fused naphthopyran compounds (a) through (i), in which representative names and structural formulas are provided.

In accordance with some embodiments, a non-limiting example of an indeno-fused naphthopyran represented by Formula (I) includes, but is not limited to, (a) 6-methoxy-7-(piperidin-1-yl)-11-(2-methoxyphenyl)-13,13-dimethyl-3-phenyl-3-(4-(4-(2-methacryloxyethyl)carbamylpiperazin-1-yl)phenyl-3H,13H-indeno[2',3':3,4]naphtho[1,2-b]pyran, which is represented by the following Formula (a),

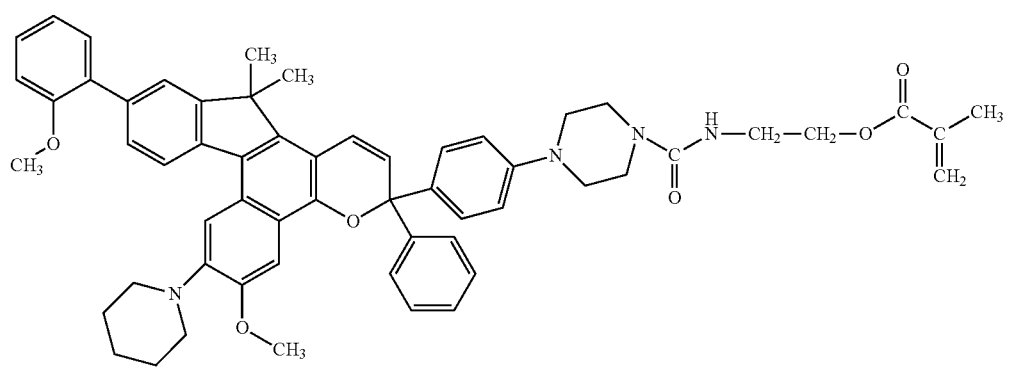

(a)

With reference to Formula (I) and Formula (a), $R^1$ is methoxy, $R^2$ is piperidin-1-yl (or piperidino), $R^3$ is 2-methoxyphenyl, $R^4$ and $R^5$ are each methyl, B is 4-(4-(2-methacryloxyethyl)carbamylpiperazin-1-yl)phenyl, and B' is phenyl.

In accordance with some embodiments, a non-limiting example of an indeno-fused naphthopyran represented by Formula (I) includes, but is not limited to, (b) 6-methoxy-7-(4-(3-((((2-(methacryloxy)ethyl)carbamoyl)methyl)piperidin-1-yl)-11-(2-methoxyphenyl)-13,13-dimethyl-3-(4-morpholinophenyl)-3-phenyl-3H,13H-indeno[2',3':3,4]naphtho[1,2-b]pyran, which is represented by the following Formula (b),

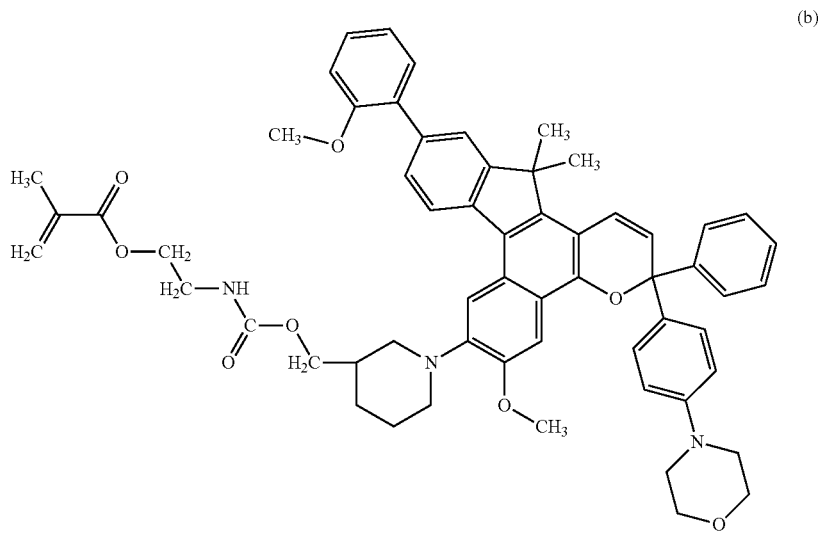 [SMILES: C=C(C)C(=O)OCCNC(=O)OCC1CCCN(c2cc3c4c(c5c(c3cc2OC)OC(c2ccccc2)(c2ccc(N3CCOCC3)cc2)C=C5)C(C)(C)c2cc(-c3ccccc3OC)ccc2-4)C1]
(b)

With reference to Formula (I) and Formula (b), $R^1$ is methoxy, $R^2$ is 7 (4 (3 ((((2-(methacryloxy)ethyl)carbamoyl)methyl)piperidin-1-yl)), $R^3$ is 2-methoxyphenyl, $R^4$ and $R^5$ are each methyl, B is phenyl, and B' is 4-morpholinophenyl.

A non-limiting example of an indeno-fused naphthopyran, in accordance with some embodiments, represented by Formula (I) includes, but is not limited to, (c) 6-methoxy-7-(piperidin-1-yl)-13,13-dimethyl-3-phenyl-3-(4-(4-(4-(2-(methacryloxy)ethoxy)-4-oxobutanoyl)piperazin-1-yl) phenyl-3H,13H-indeno[2',3':3,4]naphtho[1,2-b]pyran, which is represented by the following Formula (c),

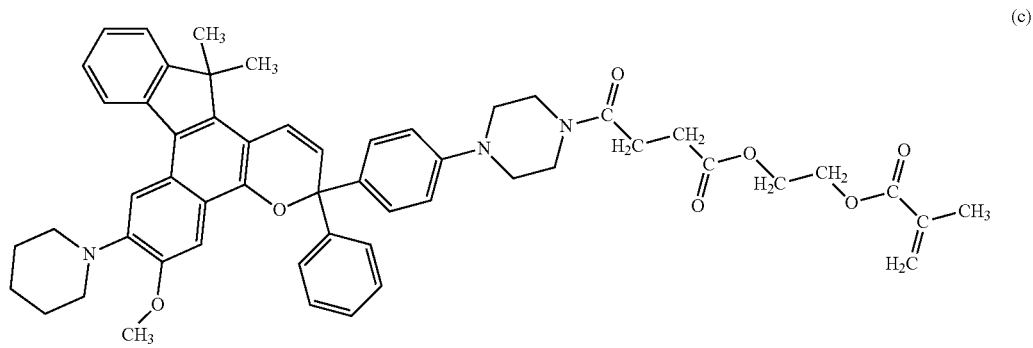 [SMILES: C=C(C)C(=O)OCCOC(=O)CCC(=O)N1CCN(c2ccc(C3(c4ccccc4)C=Cc4c5c(c6cc(N7CCCCC7)c(OC)cc6c4O3)-c3ccccc3C5(C)C)cc2)CC1]
(c)

With reference to Formula (I) and Formula (c), $R^1$ is methoxy, $R^2$ is piperidin-1-yl (or piperidino), $R^3$ is hydrogen, $R^4$ and $R^5$ are each methyl, B is 4-(4-(4-(2-(methacryloxy)ethoxy)-4-oxobutanoyl)piperazin-1-yl)phenyl, and B' is phenyl.

A further non-limiting example of an indeno-fused naphthopyran, in accordance with some embodiments, represented by Formula (I) includes, but is not limited to, (d) 6-methoxy-7-(dioctylamino)-13,13-dimethyl-3-phenyl-3-(4-(4-(4-(2-(methacryloxy)ethoxy)-4-oxobutanoyl)-3-methylpiperazin-1-yl)phenyl-3H,13H-indeno[2',3':3,4]naphtho[1,2-b]pyran, which is represented by the following Formula (d),

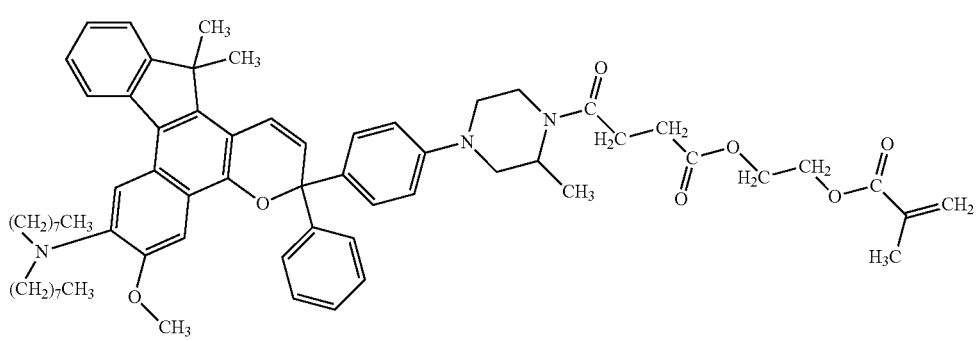

(d)

With reference to Formula (I) and Formula (d), $R^1$ is methoxy, $R^2$ is dioctylamino, $R^3$ is hydrogen, $R^4$ and $R^5$ are each methyl, B is 4-(4-(4-(2-(methacryloxy)ethoxy)-4-oxobutanoyl)-3-methylpiperazin-1-yl)phenyl, and B' is phenyl.

In accordance with some embodiments, a non-limiting example of an indeno-fused naphthopyran represented by Formula (I) includes, but is not limited to, (e) 6-methoxy-7-(octahydroisoquinolin-2(1H)-yl)-11-(tert-butyl)-13,13-dimethyl-3-phenyl-3-(4-(4-(6-acrylamidohexanoyl)-3-methylpiperazin-1-yl)phenyl-3H,13H-indeno[2',3':3,4]naphtho[1,2-b]pyran, which is represented by the following Formula (e),

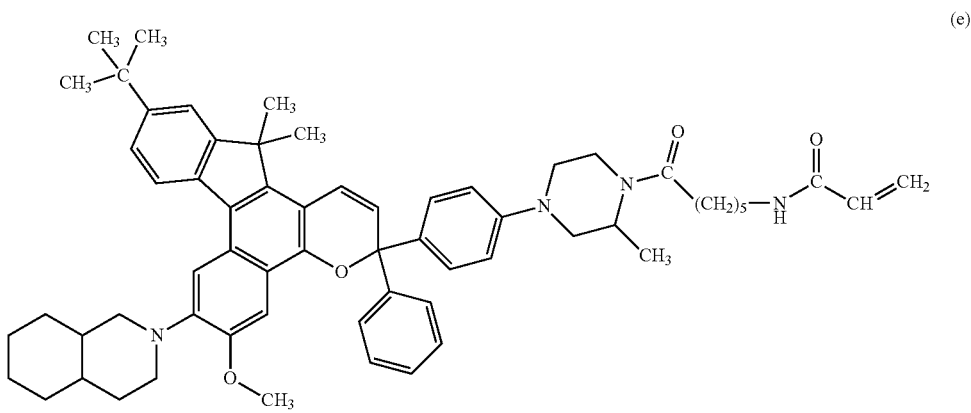

(e)

With reference to Formula (I) and Formula (e), $R^1$ is methoxy, $R^2$ is octahydroisoquinolin-2(1H)-yl, $R^3$ is tert-butyl, $R^4$ and $R^5$ are each methyl, B is 4-(4-(6-acrylamidohexanoyl)-3-methylpiperazin-1-yl)phenyl, and B' is phenyl.

In accordance with some embodiments, a non-limiting example of an indeno-fused naphthopyran represented by Formula (I) includes, but is not limited to, (f) 6 methoxy-7-(octahydroisoquinolin-2(1H)-yl)-11-(tert-butyl)-13,13-dimethyl-3-phenyl-3-(4-(4-(((5-(((2-(methacryloxy)ethyl)carbamoyl)-1,3,3-trimethylcyclohexyl)methyl)carbamyl)-3-methylpiperazin-1-yl)phenyl-3H,13H-indeno[2',3':3,4]naphtho[1,2-b]pyran, which is represented by the following Formula (f),

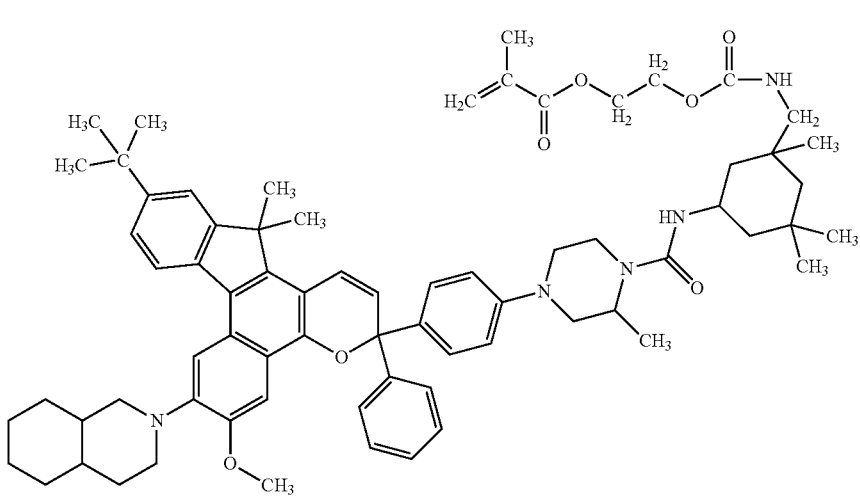

(f)

With reference to Formula (I) and Formula (f), $R^1$ is methoxy, $R^2$ is octahydroisoquinolin-2(1H)-yl, $R^3$ is tert-butyl, $R^4$ and $R^5$ are each methyl, B is 4-(4-(((5-(((2-(methacryloxy)ethyl)carbamoyl)-1,3,3-trimethylcyclohexyl)methyl)carbamyl)-3-methylpiperazin-1-yl)phenyl, and B' is phenyl.

In accordance with some embodiments, a non-limiting example of an indeno-fused naphthopyran represented by Formula (I) includes, but is not limited to, (g) 6-methoxy-7-piperidin-1-yl)-11-(tert-butyl)-13,13-dimethyl-3-phenyl-3-(4-(4-(((5-(((2-(methacryloxy)ethyl)carbamoyl)-1,3,3-trimethylcyclohexyl)methyl)carbamyl)-3-methylpiperazin-1-yl)phenyl-3H,13H-indeno[2',3':3,4]naphtho[1,2-b]pyran, which is represented by the following Formula (g),

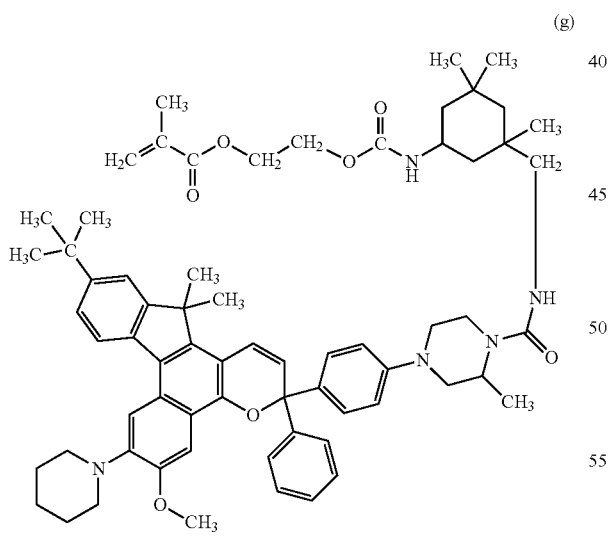

(g)

With reference to Formula (I) and Formula (g), $R^1$ is methoxy, $R^2$ is piperidin-1-yl (or piperidino), $R^3$ is tert-butyl, $R^4$ and $R^5$ are each methyl, B is 4-(4-(((5-(((2-(methacryloxy)ethyl)carbamoyl)-1,3,3-trimethylcyclohexyl)methyl)carbamyl)-3-methylpiperazin-1-yl)phenyl, and B' is phenyl.

In accordance with some embodiments, a non-limiting example of an indeno-fused naphthopyran represented by Formula (I) includes, but is not limited to, (h) 6-methoxy-7-(octahydroisoquinolin-2(1H)-yl)-11-(tert-butyl)-13,13-dimethyl-3-phenyl-3-(4-(4-(4-(2-(methacryloxy)ethoxy)-4-oxobutanoyl)3-methylpiperazin-1-yl)phenyl-3H,13H-indeno[2',3':3,4]naphtho[1,2-b]pyran, which is represented by the following Formula (h),

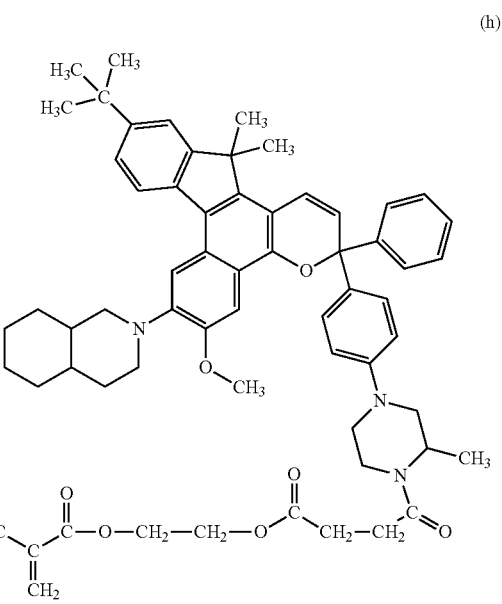

(h)

With reference to Formula (I) and Formula (h), $R^1$ is methoxy, $R^2$ is octahydroisoquinolin-2(1H)-yl, $R^3$ is tert-butyl, $R^4$ and $R^5$ are each methyl, B is phenyl, and B' is 4-(4-(4-(2-(methacryloxy)ethoxy)-4-oxobutanoyl)3-methylpiperazin-1-yl)phenyl.

In accordance with some embodiments, a non-limiting example of an indeno-fused naphthopyran represented by Formula (I) includes, but is not limited to, (i) 6-methoxy-7-(piperidin-1-yl)-1'-(tert-butyl)-13,13-dimethyl-3-phenyl-3-(4-(4-(4-(2-(methacryloxy)ethoxy)-4-oxobutanoyl)piperazin-1-yl)phenyl-3H,13H-indeno[2',3':3,4]naphtho[1,2-b]pyran, which is represented by the following Formula (i), (i)

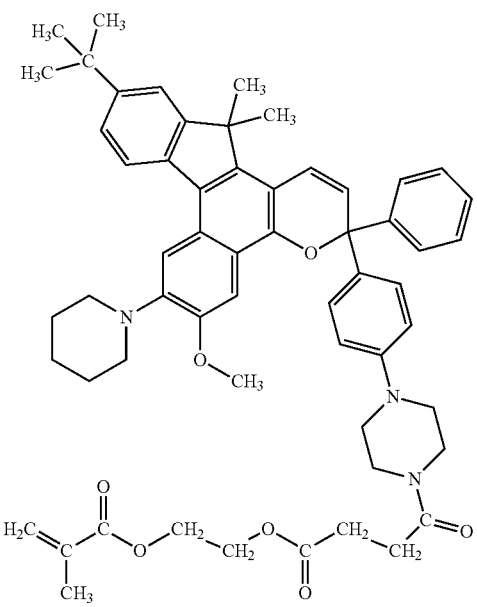

With reference to Formula (I) and Formula (i), $R^1$ is methoxy, $R^2$ is piperidin-1-yl (or piperidino), $R^3$ is tert-butyl, $R^4$ and $R^5$ are each methyl, B is phenyl, and B' is 4-(4-(4-(2-(methacryloxy)ethoxy)-4-oxobutanoyl)piperazin-1-yl)phenyl.

As previously discussed, B and B' of the indeno-fused naphthopyrans of the present invention can each be selected from an aryl group that is mono-substituted with a reactive substituent or a compatibilizing substituent. If the indeno-fused naphthopyan includes multiple reactive substituents and/or multiple compatibilizing substituents, each reactive substituent and each compatibilizing substituent can be independently chosen.

The reactive substituent and the compatibilizing substituent can each independently be represented in each case by one of:
-A'-D-E-G-J (XIII); -G-E-G-J (XVI); -D-E-G-J (XIX);
-A'-D-J (XIV); -D-G-J (XVII); -D-J (XX);
-A'-G-J (XV); -G-J (XVIII); and -A'-J (XXI).

With formulas (XIII) through (XXI), non-limiting examples of groups that -A'- can represent according to various non-limiting embodiments disclosed herein include —O—, —C(=O)—, —CH$_2$—, —OC(=O)— and —NHC(=O)—, provided that if -A'- represents —O—, -A'-forms at least one bond with -J.

Non-limiting examples of groups that -D- can represent according to various non-limiting embodiments include a diamine residue or a derivative thereof, wherein a first amino nitrogen of said diamine residue can form a bond with -A'-, or a substituent or an available position on the indeno-fused naphthopyran, and a second amino nitrogen of said diamine residue can form a bond with -E-, -G- or -J; and an amino alcohol residue or a derivative thereof, wherein an amino nitrogen of said amino alcohol residue can form a bond with -A'-, or a substituent or an available position on the indeno-fused naphthopyran, and an alcohol oxygen of said amino alcohol residue can form a bond with -E-, -G- or -J. Alternatively, according to various non-limiting embodiments disclosed herein the amino nitrogen of the amino alcohol residue can form a bond with -E-, -G- or -J, and the alcohol oxygen of the amino alcohol residue can form a bond with -A'-, or a substituent or an available position on the indeno-fused naphthopyran.

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. More particular, illustrative and non-limiting examples of diamine residues that can be used in conjunction with various non-limiting embodiments disclosed herein include the following:

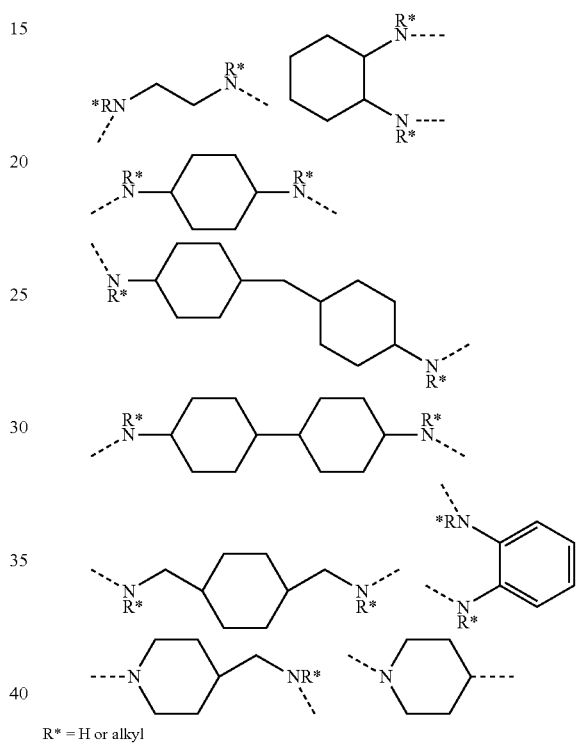

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. More particular, illustrative and non-limiting examples of amino alcohol residues that can be used in conjunction with various non-limiting embodiments disclosed herein include the following:

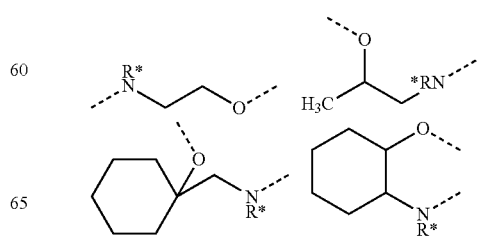

-continued

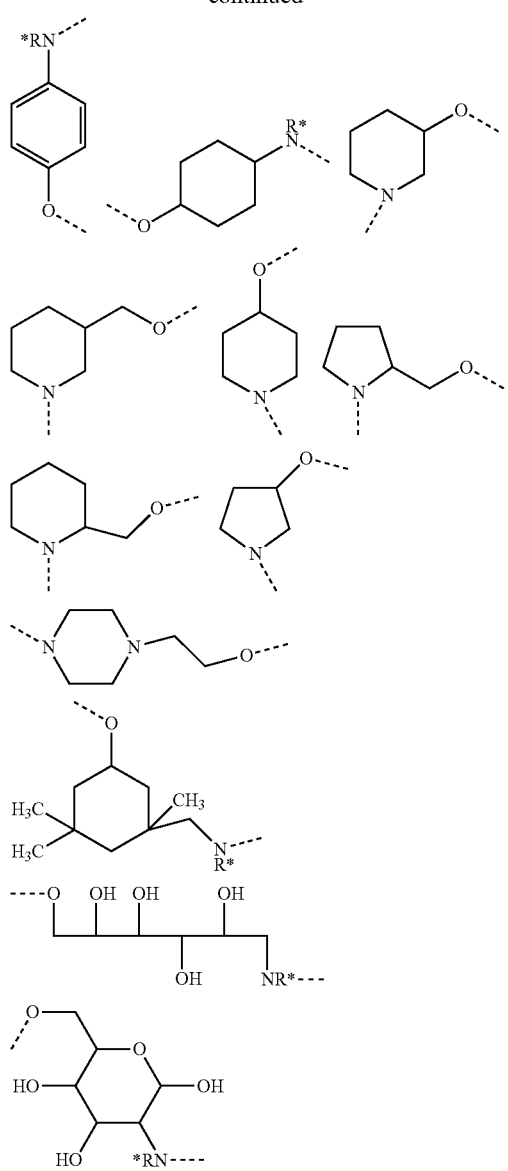

R* = H, alkyl

With continued reference to formulas (XIII) through (XXI) above, according to various non-limiting embodiments disclosed herein, -E- can represent a dicarboxylic acid residue or a derivative thereof, wherein a first carbonyl group of said dicarboxylic acid residue can form a bond with -G- or -D-, and a second carbonyl group of said dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. More particular, illustrative and non-limiting examples of dicarboxylic acid residues that can be used in conjunction with various non-limiting embodiments disclosed herein include the following:

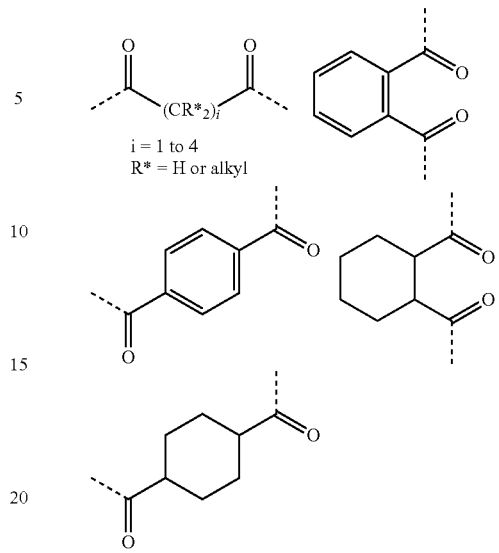

i = 1 to 4
R* = H or alkyl

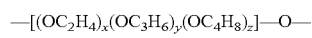

According to various non-limiting embodiments disclosed herein, -G- can represent a group represented by the following general formula, —[(OC$_2$H$_4$)$_x$(OC$_3$H$_6$)$_y$(OC$_4$H$_8$)$_z$]—O— in which x, y and z are each independently chosen and range from 0 to 50, and a sum of x, y, and z ranges from 1 to 50; a polyol residue or a derivative thereof, wherein a first polyol oxygen of said polyol residue can form a bond with -A'-, -D-, -E-, or a substituent or an available position on the indeno-fused naphthopyran, and a second polyol oxygen of said polyol can form a bond with -E- or -J; or a combination thereof, wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group -[(OC$_2$H$_4$)$_x$(OC$_3$H$_6$)$_y$(OC$_4$H$_8$)$_z$]—O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particular, illustrative and non-limiting examples of polyols from which the polyol residues that -G- can represent can be formed according to various non-limiting embodiments disclosed herein include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XIII) through (XXI), according to various non-limiting embodiments disclosed herein, -J can represent a group -K, wherein -K represents a group such as, but not limited to, $-CH_2COOH$, $-CH(CH_3)COOH$, $-C(O)(CH_2)_nCOOH$, $-C_6H_4SO_3H$, $-C_6H_{10}SO_3H$, $-C_4H_8SO_3H$, $-C_3H_6SO_3H$, $-C_2H_4SO_3H$ and $-SO_3H$, wherein "w" ranges from 1 to 18. According to other non-limiting embodiments -J can represent hydrogen that forms a bond with an oxygen or a nitrogen of linking group to form a reactive moiety such as —OH or —NH. For example, according to various non-limiting embodiments disclosed herein, -J can represent hydrogen, provided that if -J represents hydrogen, -J is bonded to an oxygen of -D- or -G-, or a nitrogen of -D-.

According to still further non-limiting embodiments, -J can represent a group -L or residue thereof, wherein -L can represent a reactive moiety. For example, according to various non-limiting embodiments disclosed herein -L can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

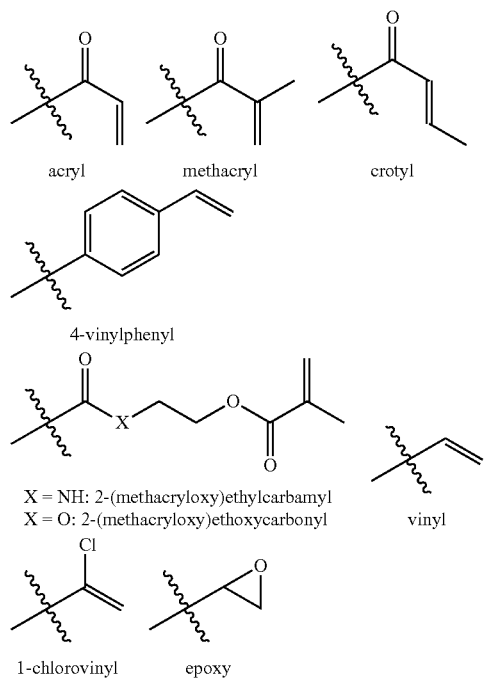

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by $q\text{-}(OH)_a$ and the residue of the polyol can be represented by the formula $-O\text{-}q\text{-}(OH)_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group -K that contains a carboxyl terminating group, -G-J can be produced by reacting one or more polyol hydroxyl groups to form the group -K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group -K that contains a sulfo or sulfono terminating group, although not limiting herein, -G-J can be produced by acidic condensation of one or more of the polyol hydroxyl groups with $HOC_6H_4SO_3H$; $HOC_5H_{10}SO_3H$; $HOC_4H_8SO_3H$; $HOC_3H_6SO_3H$; $HOC_2H_4SO_3H$; or $H_2SO_4$, respectively. Further, although not limiting herein, if -G- represents a polyol residue and -J represents a group -L chosen from acryl, methacryl, 2-(methacryloxy)ethylcarbamyl and epoxy, -L can be added by condensation of the polyol residue with acryloyl chloride, methacryloyl chloride, 2-isocyanatoethyl methacrylate or epichlorohydrin, respectively.

Additional description of reactive substituents that can be used in connection with the photochromic materials described herein is set forth at col. 5, line 42 to col. 15, line 28, in U.S. Pat. No. 7,556,750, entitled PHOTOCHROMIC MATERIALS WITH REACTIVE SUBSTITUENTS, which is hereby specifically incorporated by reference herein. Further non-limiting examples of reactive and/or compatiblizing substituents are set forth in U.S. Pat. No. 6,555,028, at col. 3, line 45 to col. 4, line 26, and U.S. Pat. No. 6,113,814 at col. 3, lines 30-64, which disclosures are hereby specifically incorporated by reference herein.

The indeno-fused naphthopyran compounds of the present invention can be prepared by art-recognized methods. With some embodiments, the indeno-fused naphthopyran compounds of the present invention can be synthesized in accordance with the description provided in U.S. Pat. No. 6,296,785, at column 10, line 52 through column 29, line 18, which disclosure is incorporated herein by reference. With some further embodiments, the indeno-fused naphthopyran compounds of the present invention can be synthesized in accordance with the description provided in U.S. Pat. No. 7,527,754 B2 at column 13, line 52 through column 14, line 62, which disclosure is incorporated herein by reference. With some additional further embodiments, the indeno-fused naphthopyran compounds of the present invention can be synthesized in accordance with the description provided in U.S. Pat. No. 5,645,767, at column 5, line 6 through column 11, line 31, which disclosure is incorporated herein by reference.

With some embodiments, the indeno-fused naphthopyran compounds of the present invention are prepared in accordance with the synthetic descriptions provided in the examples further herein.

With some embodiments, the indeno-fused naphthopyran compounds of the present invention can each be used alone, or in combination with other photochromic compounds. For example, the indeno-fused naphthopyran compounds of the present invention can be used in conjunction with other photochromic compounds having activated absorption maxima within the range of 300 to 1000 nanometers. Further, the indeno-fused naphthopyran compounds according to the present invention can be used in conjunction with a complementary conventional polymerizable or a compatiblized photochromic compound, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

The indeno-fused naphthopyran compounds of the present invention can be used in combination with a mixture of other photochromic compounds. For example, although not limiting herein, mixtures of photochromic compounds can be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Examples of classes of other photochromic compounds that can be used in combination with the indeno-fused naphthopyrans of the present invention, include, but are not limited to, indeno-fused naphthopyrans, naphtho[1,2-b]pyrans, naphtho[2,1-b]pyrans, spirofluoreno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof.

Non-limiting examples of photochromic pyrans that can be used in combination with the indeno-fused naphthopyrans of the present invention, include, but are not limited to, benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. Further examples of naphthopyrans and complementary organic photochromic compounds are described in U.S. Pat. No. 5,658,501, which are hereby specifically incorporated by reference herein. Spiro(indoline)pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of photochromic oxazines that can be used in combination with the indeno-fused naphthopyrans of the present invention, include, but are not limited to, benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine. Non-limiting examples of photochromic fulgides that can be used in combination with the indeno-fused naphthopyrans of the present invention, include, but are not limited to: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

The present invention also relates to photochromic articles that include one or more indeno-fused naphthopyrans of the present invention represented by Formula (I).

In accordance with further embodiments of the present invention, the photochromic articles of the present invention can be selected from ophthalmic articles or elements, display articles or elements, windows, mirrors, packaging material such as shrinkwrap, active liquid crystal cell articles or elements, and passive liquid crystal cell articles or elements.

Examples of ophthalmic articles or elements include, but are not limited to, corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

Examples of display articles, elements and devices include, but are not limited to, screens, monitors, and security elements, including without limitation, security marks and authentication marks.

Examples of windows include, but are not limited to, automotive and aircraft transparencies, filters, shutters, and optical switches.

With some embodiments, the photochromic article can be a security element. Examples of security elements include, but are not limited to, security marks and authentication marks that are connected to at least a portion of a substrate, such as: access cards and passes, e.g., tickets, badges, identification or membership cards, debit cards, etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

With further embodiments, the security element can be connected to at least a portion of a substrate chosen from a transparent substrate and a reflective substrate. Alternatively, according to further embodiments in which a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Additionally or alternatively, the security element can be connected to at least a portion of a substrate chosen from untinted substrates, tinted substrates, photochromic substrates, tinted-photochromic substrates, linearly polarizing, circularly polarizing substrates, and elliptically polarizing substrates.

Furthermore, security elements according to the aforementioned embodiments can further include one or more other coatings or films or sheets to form a multi-layer reflective security element with viewing angle dependent characteristics, such as described in U.S. Pat. No. 6,641,874.

Photochromic articles according to the present invention, such as optical elements, can include a substrate and a photochromic material that includes the indeno-fused naphthopyran compound or compounds according to the present invention, in which the photochromic material is connected to at least a portion of the substrate. As used herein, the term "connected to" means associated with, either directly, or indirectly by means of another material or structure.

Photochromic articles according to the present invention can include, as discussed above, a substrate that can include one or more polymeric compounds. The indeno-fused naphthopyran compounds of the present invention can be incorporated into at least a portion of the polymeric material of the substrate; or by incorporating the indeno-fused naphthopyran compound(s) into at least a portion of the oligomeric or monomeric material from which the substrate is formed. For example, according to one non-limiting embodiment, the indeno-fused naphthopyran compound can be incorporated into the polymeric material of the substrate by a cast-in-place method or by imbibition. The imbibition and the cast-in-place methods are discussed in further detail herein below.

With the imbibition method, the photochromic compound is typically diffused into the polymeric material of a previously formed or fabricated article, such as a substrate or previously applied coating/film. Imbibition can be performed by immersing the polymeric material of a previously formed or fabricated article in a solution containing the photochromic compound, with or without heating. Thereafter, although not required, the photochromic compound can be bonded with the polymeric material (e.g., of the substrate or coating).

With cast-in-place methods, the photochromic compound(s) can be mixed with: a polymer and/or oligomer composition in solution or melt form; or monomer composition in liquid form, so as to form a castable photochromic composition. The castable photochromic composition is then typically introduced into the cavity of a mold (e.g., a lens mold). The castable photochromic composition is then set within the mold so as to form a photochromic article.

With photochromic articles according to the present invention that include a substrate, a photochromic compound(s) can be included in a coating that is connected to at least a portion of the substrate. The substrate can be a polymeric substrate or an inorganic substrate (such as, but not limited to, a glass substrate). The photochromic compound(s) can be incorporated into at least a portion of a coating composition prior to application of the coating composition to the substrate. Alternatively, a coating composition can be applied to the substrate, at least partially set, and thereafter the photochromic compound(s) can be imbibed into at least a portion of the coating. As used herein, the terms "set" and "setting" include, without limitation, curing, polymerizing, cross-linking, cooling, and drying.

Photochromic articles according to the present invention can be formed by art-recognized in-mold coating (or in-mold casting) methods. With in-mold coating methods, a photochromic coating composition that includes a photochromic indeno-fused naphthopyran compound(s) of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the photochromic materials according to various non-limiting embodiments disclosed herein can be employed are set forth in U.S. Pat. No. 6,068,797 at col. 7, line 50 to col. 19, line 42, which disclosure is hereby specifically incorporated by reference herein.

Photochromic articles according to the present invention can also be formed by art-recognized over-mold methods. Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic coating composition is introduced (e.g., injected) into the interior space. The photochromic coating compositions include one or more indeno-fused naphthopyran compounds of the present invention.

Photochromic articles according to the present invention can also be formed by art-recognized lamination methods. With lamination methods, a film comprising the photochromic indeno-fused naphthopyran compound(s) according to the present invention can be adhered or otherwise connected to a portion of the substrate, with or without an adhesive and/or the application of heat and pressure. Thereafter, if desired, a second substrate can be applied over the first substrate and the two substrates can be laminated together (i.e., by the application of heat and pressure) to form an element wherein the film comprising the photochromic compound is interposed between the two substrates. Methods of forming films comprising the photochromic indeno-fused naphthopyran compounds of the present invention can include for example and without limitation, combining a photochromic indeno-fused naphthopyran compound with a polymeric solution or oligomeric solution or mixture, casting or extruding a film therefrom, and, if required, at least partially setting the film. Additionally or alternatively, a film can be formed (with or without a photochromic compound) and then subsequently imbibed with the photochromic compound.

Coating compositions that include one or more indeno-fused naphthopyran compounds represented by Formula (I), of the present invention can be connected to at least a portion of the substrate of the photochromic article by art-recognized methods, such as applying a coating composition that includes the photochromic indeno-fused naphthopyran compound(s) to at least a portion of a surface of the substrate, and at least partially setting the coating composition. Non-limiting classes and examples of coating compositions that include one or more indeno-fused naphthopyran compounds represented by Formula (I), are described in further detail herein. Additionally or alternatively, the coating that includes the photochromic indeno-fused naphthopyran compound(s) can be connected to the substrate, for example, through one or more additional coatings. For example, while not limiting herein, according to various non-limiting embodiments, an additional coating composition can be applied to a portion of the surface of the substrate, at least partially set, and thereafter the coating composition that includes the photochromic compound(s) can be applied over the additional coating and at least partially set. Non-limiting and art-recognized methods of applying coatings compositions to substrates are discussed herein below.

Examples of additional coatings and films that can be used in conjunction with the photochromic coatings and articles according to the present invention, include, but are not limited to: primer coatings and films (which typically reside under the photochromic coating); protective coatings and films (which are typically applied over the photochromic coating), including transitional coatings and films and abrasion resistant coatings and films; anti-reflective coatings and films; conventional photochromic coatings and films; polarizing coatings and films; and combinations thereof. As used herein the term "protective coating or film" refers to coatings or films that can prevent wear or abrasion, provide a transition in properties from one coating or film to another, protect against the effects of polymerization reaction chemicals and/or protect against deterioration due to environmental conditions such as moisture, heat, ultraviolet light, oxygen, etc.

As used herein, the term "transitional coating and film" means a coating or film that aids in creating a gradient in properties between two coatings or films, or a coating and a film. For example, although not limiting herein, a transitional coating can aid in creating a gradient in hardness between a relatively hard coating and a relatively soft coating. Non-limiting examples of transitional coatings include radiation-cured, acrylate-based thin films as described in U.S. Patent Application Publication 2003/0165686 at paragraphs 79-173, which are hereby specifically incorporated by reference herein.

As used herein the term "abrasion resistant coating and film" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion resistant coatings include, for example, abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof.

Non-limiting examples of antireflective coatings and films include a monolayer, multilayer or film of metal oxides, metal fluorides, or other such materials, which can be deposited onto the articles disclosed herein (or onto films that are applied to the articles), for example, through vacuum deposition, sputtering, etc. Non-limiting examples of conventional photochromic coatings and films include, but are not limited to, coatings and films comprising conventional photochromic materials. Non-limiting examples of polarizing coatings and films include, but are not limited to, coatings and films comprising dichroic compounds that are known in the art.

Additional coating compositions (e.g., primers and overcoats) that can be used with photochromic coating compositions according to the present invention and/or to form photochromic articles according to the present invention, can be applied to/formed: on a substrate prior to application of the photochromic coating; and/or over a previously applied photochromic coating. For example, a primer coating can be formed on the substrate prior to applying a photochromic coating composition according to the present invention. Additionally or alternatively, an additional coating or film can be applied (e.g., as an over-coat or over-coating) at least partially over a previously applied photochromic coating composition according to the present invention. For example, a transitional coating can be formed over a previously applied photochromic coating composition according to the present invention, and an abrasion resistant coating can then be applied over the transitional coating.

In accordance with various non-limiting embodiments of the present invention, there is provided a photochromic composition comprising: an organic material, the organic material being at least one of polymeric material, an oligomeric material and a monomeric material; and one or more indeno-fused naphthopyrans according to any of the non-limiting embodiments as set forth above incorporated into at least a portion of the organic material. According to various non-limiting embodiments disclosed herein, the indeno-fused naphthopyran(s) can be incorporated into a portion of the organic material by at least one of blending and bonding the indeno-fused naphthopyran(s) with the organic material or a precursor thereof. As used herein with reference to the incorporation of indeno-fused naphthopyran(s) into an organic material, the terms "blending" and "blended" mean that the indeno-fused naphthopyran is intermixed or intermingled with the at least a portion of the organic material, but not bonded to the organic material. Further, as used herein with reference to the incorporation of the indeno-fused naphthopyran into an organic material, the terms "bonding" or "bonded" mean that the indeno-fused naphthopyran is linked to a portion of the organic material or a precursor thereof. For example, although not limiting herein, the indeno-fused naphthopyran can be linked to the organic material through a reactive substituent.

In accordance with some non-limiting embodiments of the present invention, when the organic material is a polymeric material, the indeno-fused naphthopyran can be incorporated into at least a portion of the polymeric material or at least a portion of the monomeric material or oligomeric material from which the polymeric material is formed. For example, indeno-fused naphthopyrans according to various non-limiting embodiments disclosed herein that have a reactive substituent can be bonded to an organic material such as a monomer, oligomer, or polymer having a group with which a reactive moiety can be reacted, or the reactive moiety can be reacted as a co-monomer in the polymerization reaction from which the organic material is formed, for example, in a co-polymerization process.

As discussed above, the photochromic compositions according to various non-limiting embodiments disclosed herein can include an organic material chosen from a polymeric material, an oligomeric material and/or a monomeric material. Examples of polymeric materials that can be used in conjunction with various non-limiting embodiments disclosed herein include, without limitation: polymers of bis (allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly (vinyl alcohol); poly(vinyl chloride); poly(vinylidene chloride); polyurethanes; polythiourethanes; thermoplastic polycarbonates; polyesters; poly(ethylene terephthalate); polystyrene; poly(alpha-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Further, according to various non-limiting embodiments in which transparency of the photochromic composition is desired, the organic material can be a transparent polymeric material. For example, according to various non-limiting embodiments, the polymeric material can be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to one non-limiting embodiment, the polymeric material can be an optical resins sold by PPG Industries, Inc. under the CR-designation, e.g., CR-307, CR-407, and CR-607.

In accordance with some embodiments, the organic material can be a polymeric material which is chosen from poly (carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

With some further embodiments, the photochromic composition of the present invention further includes at least one of, a complementary photochromic material (including one or more of those other photochromic materials and compounds described previously herein), a photoinitiator, a thermal initiator, a polymerization inhibitor, a solvent, a light stabilizer, a heat stabilizer, a mold release agent, a rheology control agent, a leveling agent, a free radical scavenger, and an adhesion promoter.

In accordance with some embodiments, the photochromic composition according to the present invention is a photochromic coating composition. Photochromic coating compositions according to some embodiments of the present invention include: an indeno-fused naphthopyran according to the present invention, such as described previously herein with regard to Formula (I); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. In an embodiment, the photochromic coating composition is a curable or thermosetting coating composition.

The curable resin composition of the curable photochromic coating compositions, according to some embodiments of the present invention, include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance and hardness.

Examples of curable resin compositions that can be used with the curable photochromic coating compositions according to the present invention include, but are not limited to: curable resin compositions comprising epoxide functional polymer (e.g., (meth)acrylic polymers containing residues of glycidyl (meth)acrylate and epoxide reactive crosslinking agent (e.g., containing active hydrogens, such as hydroxyls, thiols and amines); and curable resin compositions comprising hydroxy functional polymer and capped (or blocked) isocyanate functional crosslinking agent.

In an embodiment, the curable resin composition of the photochromic coating composition of the present invention is a curable urethane (or polyurethane) resin composition. Curable urethane resin compositions useful in the photochromic coating compositions of the present invention typically include: an active hydrogen functional polymer, such as a hydroxy functional polymer; and a capped (or blocked) isocyanate functional crosslinking agent. Hydroxy functional polymers that can be used in such compositions include, but are not limited to, art-recognized hydroxy functional vinyl polymers, hydroxy functional polyesters, hydroxy functional polyurethanes and mixtures thereof.

Vinyl polymers having hydroxy functionality can be prepared by free radical polymerization methods that are known to those of ordinary skill in the art. In an embodiment of the present invention, the hydroxy functional vinyl polymer is prepared from a majority of (meth)acrylate monomers and is referred to herein as a "hydroxy functional (meth)acrylic polymer."

Hydroxy functional polyesters useful in curable photochromic coating compositions comprising capped isocyanate functional crosslinking agent can be prepared by art-recognized methods. Typically, diols and dicarboxylic acids or diesters of dicarboxylic acids are reacted in a proportion such that the molar equivalents of hydroxy groups is greater than that of carboxylic acid groups (or esters of carboxylic acid groups) with the concurrent removal of water or alcohols from the reaction medium.

Hydroxy functional urethanes can be prepared by art-recognized methods, for example, as previously described herein. Typically one or more difunctional isocyanates are reacted with one or more materials having two active hydrogen groups (e.g., diols or dithiols), such that the ratio of active hydrogen groups to isocyanate groups is greater than 1, as is known to the skilled artisan.

By "capped (or blocked) isocyanate crosslinking agent" is meant a crosslinking agent having two or more capped isocyanate groups that can decap (or deblock) under cure conditions, e.g., at elevated temperature, to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer).

It is desirable that the capping group of the capped isocyanate crosslinking agent not adversely affect the curable photochromic coating composition upon decapping from the isocyanate (i.e., when it becomes a free capping group). For example, it is desirable that the free capping group neither become trapped in the cured film as gas bubbles nor excessively plasticize the cured film. Capping groups useful in the present invention preferably have the characteristics of being nonfugitive or capable of escaping substantially from the forming coating prior to its vitrification. Typically, the free capping groups escape substantially from the forming (e.g., curing) coating prior to its vitrification.

Classes of capping groups of the capped isocyanate crosslinking agent can be selected from: hydroxy functional compounds, e.g., linear or branched $C_2$-$C_8$ alcohols, ethylene glycol butyl ether, phenol and p-hydroxy methylbenzoate; 1H-azoles, e.g., 1H-1,2,4-triazole and 1H-2,5-dimethylpyrazole; lactams, e.g., e-caprolactam and 2-pyrrolidinone; ketoximes, e.g., 2-propanone oxime and 2-butanone oxime. Other suitable capping groups include, morpholine, 3-aminopropyl morpholine and N-hydroxy phthalimide.

The isocyanate or mixture of isocyanates of the capped isocyanate crosslinking agent has two or more isocyanate groups (e.g., 3 or 4 isocyanate groups). Examples of suitable isocyanates that can be used to prepare the capped isocyanate crosslinking agent include, monomeric diisocyanates, e.g., α,α'-xylylene diisocyanate, α, α, α', α'-tetramethylxylylene diisocyanate and 1-isocyanato-3-isocyanatomethyl-3,5,5-trimethylcyclohexane (isophorone diisocyanate or IPDI), and dimers and trimers of monomeric diisocyanates containing isocyanurate, uretidino, biruet or allophanate linkages, e.g., the trimer of IPDI.

The capped isocyanate crosslinking agent can also be selected from oligomeric capped isocyanate functional adducts. As used herein, by "oligomeric capped polyisocyanate functional adduct" is meant a material that is substantially free of polymeric chain extension. Oligomeric capped polyisocyanate functional adducts can be prepared by art-recognized methods from, for example, a compound containing three or more active hydrogen groups, e.g., trimethylolpropane (TMP), and an isocyanate monomer, e.g., 1-isocyanato-3,3,5-trimethyl-5-isocyanatomethylcyclohexane (IPDI), in a molar ratio of 1:3, respectively. In the case of TMP and IPDI, by employing art-recognized starved feed and/or dilute solution synthesis techniques, an oligomeric adduct having an average isocyanate functionality of 3 can be prepared (e.g., "TMP-3IPDI"). The three free isocyanate groups per TMP-3IPDI adduct are then capped with a capping group, e.g., a linear or branched $C_2$-$C_8$ alcohol.

To catalyze the reaction between the isocyanate groups of the capped polyisocyanate crosslinking agent and the hydroxy groups of the hydroxy functional polymer, one or more catalysts are typically present in the curable photochromic coating composition in amounts of from, for example, 0.1 to 5 percent by weight, based on total resin solids of the composition. Classes of useful catalysts include but are not limited to, metal compounds, in particular, organic tin compounds, e.g., tin(II) octanoate and dibutyltin(IV) dilaurate, and tertiary amines, e.g., diazabicyclo[2.2.2]octane.

Curable photochromic coating compositions according to the present invention, which include hydroxy functional polymer and capped isocyanate functional crosslinking agent, typically have present therein hydroxy functional polymer in an amount of from 55 percent to 95 percent by weight, based on total resin solids weight of the composition, e.g., from 75 percent to 90 percent by weight, based on total resin solids weight of the composition. The capped isocyanate functional crosslinking agent is typically present in the curable resin composition in an amount corresponding to the balance of these recited ranges, i.e., 5 to 45, particularly 10 to 25, percent by weight.

Curable photochromic coating compositions according to the present invention, which include hydroxy functional polymer and capped isocyanate functional crosslinking agent, typically have present therein hydroxy functional polymer in an amount of from 55 percent to 95 percent by weight, based on total resin solids weight of the composition, e.g., from 75 percent to 90 percent by weight, based on total resin solids weight of the composition. The capped isocyanate functional crosslinking agent is typically present in the curable resin composition in an amount corresponding to the balance of these recited ranges, i.e., 5 to 45, particularly 10 to 25, percent by weight.

Photochromic coating compositions according to the present invention can, with some embodiments, optionally further include a solvent. Examples of suitable solvents include, but art not limited to, acetates, alcohols, ketones, glycols, ethers, aliphatics, cycloaliphatics and aromatics. Examples of acetates include, but are not limited to, ethyl acetate, butyl acetate, and glycol acetate. Examples of ketones include, but are not limited to, methyl ethyl ketone and methyl-N-amyl ketone. Examples of aromatics include, but are not limited to, are toluene, naphthalene and xylene. In an embodiment, one or more solvents are added to each of the first reactant and the second reactant. Suitable solvent blends can include, for example, one or more acetates, propanol and its derivatives, one or more ketones, one or more alcohols and/or one or more aromatics. If present, the solvent is typically present in an amount of from 5 to 60 percent by weight, or 5 to 40 percent by weight, or 10 to 25 percent by weight, based on the total weight of the photochromic coating composition (inclusive of the solvent weight).

Curable photochromic coating compositions according to the present invention can, with some embodiments, optionally contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from Ciba-Geigy under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can, with some embodiments, further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

Indeno-fused naphthopyran compounds according to the present invention can be used in amounts (or ratios) such that the compositions, organic material or substrate (e.g., photochromic articles and photochromic coatings) into which the indeno-fused naphthopyran compounds are incorporated or otherwise connected exhibits desired optical properties. For example, the amount and types of indeno-fused naphthopyran compounds can be selected such that the composition, organic material or substrate is clear or colorless when the indeno-fused naphthopyran compound is in the closed-form (e.g., in the bleached or unactivated state), and can exhibit a desired resultant color when the indeno-fused naphthopyran is in the open-form (e.g., when activated by actinic radiation). The precise amount of the indeno-fused naphthopyran that is utilized in the various photochromic compositions and articles described herein is not critical provided that a sufficient amount is used to produce the desired effect. The particular amount of the indeno-fused naphthopyran compound used can depend on a variety of factors, such as but not limited to, the absorption characteristics of the indeno-fused naphthopyran compound, the color and intensity of the color desired upon activation, and the method used to incorporate or connect the indeno-fused naphthopyran compound (or a photochromic material containing same) to the substrate.

Photochromic compositions according to some embodiments of the present invention can include one or more indeno-fused naphthopyran compounds according to the present invention represented by Formula (I), in an amount of from 0.01 to 40 weight percent, or from 0.05 to 15, or from 0.1 to 5 weight percent, based on the weight of the photochromic composition. For purposes of further non-limiting illustration, the amount of the indeno-fused naphthopyran compounds represented by Formula (I) that is incorporated into an organic material can range, with some embodiments, from 0.01 to 40 weight percent, or from 0.05 to 15, or from 0.1 to 5 weight percent, based on the weight of the organic material.

The present invention is more particularly described in the following examples, which are intended to be illustrative only, since numerous modifications and variations therein will be apparent to those skilled in the art. Unless otherwise specified, all parts and all percentages are by weight.

EXAMPLES

In Part 1 of the Examples, the synthesis procedures used to make photochromic materials according to various non-limiting embodiments disclosed herein are set forth in Examples 1-9. Part 2 provides a description of the photochromic performance testing and results for Examples 1-9.

Part 1

Synthesis Procedures

Example 1

Step 1

To a 500 mL single-neck flask was added 2,3-dimethoxy-7,7-dimethyl-9-bromo-7H-benzo[C]fluoren-5-ol (10 g) prepared according to the first five steps of example 1 in US 2006/0226402 which is included herein as reference, 2-methoxyphenylboronic acid (4.3 g), sodium carbonate (5.9 g), dimethyl ether (120 mL) and water (24 mL). The mixture was purged with $N_2$ for 15 minutes. Tetrakis(triphenylphosphine) palladium(0) (0.6 g) was added to the mixture. The reaction mixture was heated to reflux for 18 hours. The mixture was cooled to room temperature and poured into water (180 mL). The resulting mixture was extracted with ethyl acetate (100 mL). The top layer was dried over sodium sulfate and then condensed to lesser volume. Solid 2,3-dimethoxy-7,7-dimethyl-9-(2-methoxyphenyl)-7H-benzo[C]fluoren-5-ol (10 g) was obtained by recrystallization from solution in t-butyl methyl ether/hexanes.

Step 2

To a 500 mL one-neck flask was added the product from Step 1 (10 g), piperidine (5.2 mL and anhydrous tetrahydrofuran (150 mL). n-Butyl lithium in hexane solution (2.5M, 35 mL) was dropped to the mixture through addition funnel slowly. The reaction mixture was stirred at room temperature for 3 hours. The mixture was poured into cold aqueous hydrochloric acid (10%, 60 mL). The resulting mixture was extracted with ethyl acetate (200 mL) and the recovered top layer was filtered through a silica gel plug using ethyl acetate and hexane mixture as eluent. All silica gel plug and chromatography mentioned herein was carried out using ethyl acetate and hexanesmixture as eluent if not specified. Solid 2-(piperidin-1-yl)-3-methoxy-7,7-dimethyl-9-(2-methoxyphenyl)-7H-benzo[C]fluoren-5-ol (10 g) was obtained by re-crystallization from solution in ethyl acetate/hexanes.

Step 3

To a 500 mL one-neck flask was added 4-fluorobenzophenone (35 g), piperazine (13 g), potassium carbonate (22 g) and dimethyl sulfoxide (100 mL). The reaction mixture was heated to 100° C. for 20 hours. The mixture was cooled to room temperature and poured into water (400 mL). The mixture was extracted with chloroform (200 mL) and the recovered bottom layer was dried over sodium sulfate. The solvent was removed and the product was dried in vacuum oven at 60° C. for 6 hours to afford 40 g of waxy 4-piperazinobenzophenone.

Step 4

To a 500 mL beaker was added the product from Step 3 (30 g) and anhydrous dimethylformamide (50 mL). Sodium acetylide xylene slurry (22 wt %, 90 g) was dropped to the mixture through addition funnel slowly. The reaction mixture was stirred with a glass stirring bar for 10 minutes. The mixture was poured into water (400 mL). The resulting mixture was extracted with ethyl acetate (200 mL). The recovered top layer was filtered through a silica gel plug using ethyl acetate and methanol mixture as eluent. Solid product was obtained by recrystallization from condensed major fraction. The solid was filtered off and dried in vacuum oven at 60° C. for 3 hours to afford 17 g of 1-phenyl-1-(4-piperazinophenyl)-2-propyn-1-ol.

Step 5

To a 500 mL one-neck flask was added the product from Step 4 (17 g), 4-hydroxy-5,6-di-t-butyltoluene (0.05 g) and anhydrous tetrahydrofuran (100 mL). 2-Isocyanatoethyl methacrylate (9 mL) was dropped to the mixture through addition funnel slowly. The reaction mixture was heated to reflux for 1 hour. The mixture was condensed to lesser volume and the residue solution was filtered through a silica gel plug. The crude product (1-phenyl-1-(4-(4-(2-methacryloxyethyl)carbamylpiperazin-1-yl)phenyl)-2-propyn-1-ol) was obtained as an oily residue and it was used as is in next step without further purification.

Step 6

To a 250 mL one-neck flask was added the product from Step 2 (10 g), pyridinium p-toluenesulfonate (0.7 g), trimethyl orthoformate (8 mL) and 1,2-dichloroethane (150 mL). The reaction mixture was heated to reflux. The product from Step 5 (10 g) was added to the mixture in portions. Heating was stopped after 4 hours and the reaction mixture was condensed to lesser volume. The residue was filtered through a silica gel plug. Solid product was obtained by recrystallization from condensed major fractions. The solid was filtered off and dried in vacuum oven for 3 hours to afford 14 g of off-white solid. NMR analysis indicated the structure was consistent with 6-methoxy-7-(piperidin-1-yl)-11-(2-methoxyphenyl)-13,13-dimethyl-3-phenyl-3-(4-(4-(2-methacryloxyethyl)carbamylpiperazin-1-yl)phenyl-3H,13H-indeno[2',3':3,4]naphtho[1,2-b]pyran shown in the following graphic formula:

mixture slowly. The reaction mixture was heated to reflux for 4 hours. The mixture was poured into cold aqueous hydrochloric acid (10%, 60 mL). The mixture was extracted with ethyl acetate (200 mL) and the recovered top layer was filtered through a silica gel plug. The major product (2-(3-hydroxymethylpiperidin)-1-yl)-3-methoxy-7,7-dimethyl-9-(2-methoxyphenyl)-7H-benzo[C]fluoren-5-ol (33 g) was obtained as foamy solid after dried under vacuum.

Step 2

To a 250 mL one-neck flask was added the product from Step 1 (7 g), dodecyl benzene sulfonic acid (0.6 g) and chloroform (70 mL). The mixture was heated to 55° C. The product of Step 1 of Example 1 in U.S. Pat. No. 5,458,814, 1-phenyl-1-(4-morpholinophenyl)-2-propyn-1-ol which is included herein as reference, was added to the mixture in portions until no product from Step 1 was observed by TLC analysis. Heating was stopped and the reaction mixture was condensed to lesser volume and the residue was filtered through a silica gel plug. The major fraction was condensed and dried under vacuum to afford the product, 6-methoxy-7-(3-hydroxymethyl)piperidin-1-yl)-11-(2-methoxyphenyl)-13,13-dimethyl-3-(4-morpholinophenyl)-3-phenyl-3H,13H-indeno[2',3',4]naphtho[1,2-b]pyran as foamy solid (9 g).

Step 3

To a 500 mL one-neck flask was added the product from Step 2 (9 g), 4-hydroxy-5,6-di-t-butyltoluene (0.05 g), 2-isocyanatoethyl methacrylate (3 mL) and ethyl acetate (100 mL). Dibutyltin dilaurate (0.05 g) was added to the mixture. The reaction mixture was heated to reflux for 30 minutes. Methanol (5 mL) was added to the mixture and the mixture was condensed to lesser volume. The residue solution was

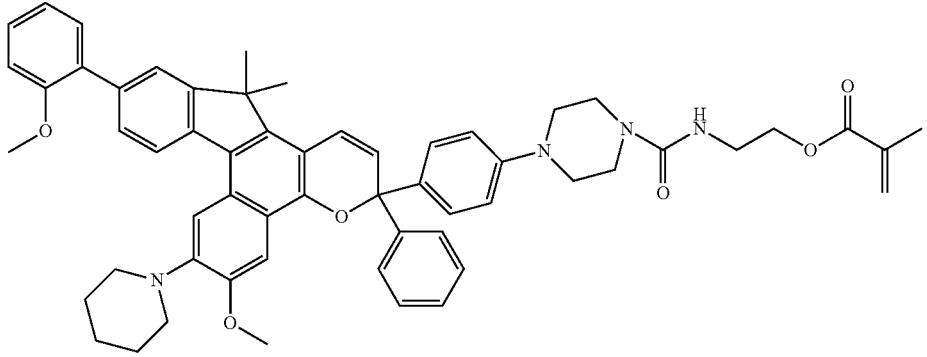 [SMILES: C=C(C)C(=O)OCCNC(=O)N1CCN(c2ccc(C3(c4ccccc4)C=Cc4c5c(c6cc(N7CCCCC7)c(OC)cc6c4O3)-c3ccc(-c4ccccc4OC)cc3C5(C)C)cc2)CC1]

Example 2

Step 1

To a 500 mL one-neck flask was added the solid product from Step 1 of Example 1 (30 g), 3-hydroxymethylenepiperidine (12 g) and anhydrous tetrahydrofuran (200 mL). n-Butyl lithium in hexane solution (2.5M, 10 mL) was dropped to the purified by a silica gel column and the major fraction was condensed to afford the product as purple foamy solid (8 g). NMR analysis indicated the structure was consistent with 6-methoxy-7-(4-(3-((((2-(methacryloxy)ethyl)carbamoyl)oxy)methyl)piperidin-1-yl)-11-(2-methoxyphenyl)-13,13-dimethyl-3-(4-morpholinophenyl)-3-phenyl-3H,13H-indeno[2',3':3,4]naphtho[1,2-b]pyran as shown in the following graphic formula:

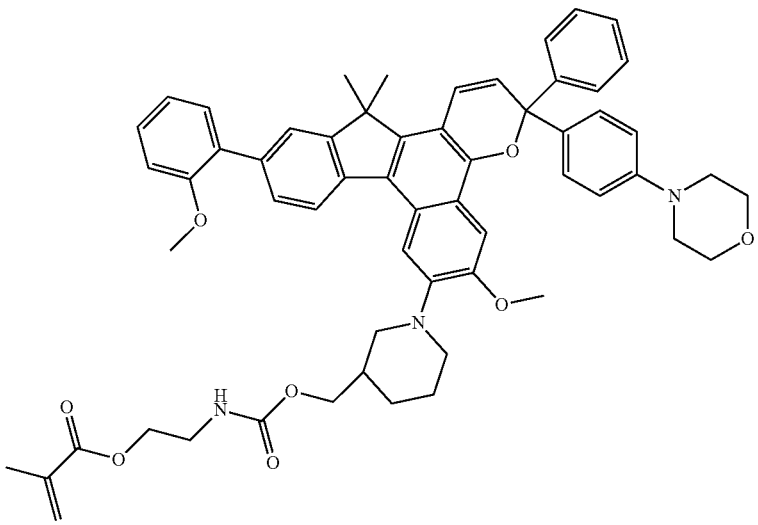 [SMILES: C=C(C)C(=O)OCCNC(=O)OCC1CCCN(c2cc3c4c(c5c(c3cc2OC)OC(c2ccccc2)(c2ccc(N3CCOCC3)cc2)C=C5)C(C)(C)c2cc(-c3ccccc3OC)ccc2-4)C1]

Example 3

Step 1

To an oven-dried 500 mL one-neck flask was added the product of Step 3, Example 1, of U.S. Pat. No. 6,296,785B1, 2,3-dimethoxy-7,7-dimethyl-7H-benzo[C]fluoren-5-ol (10 g) which is included herein as reference, piperidine (5.2 mL) and anhydrous tetrahydrofuran (150 mL). n-Butyl lithium in hexane solution (2.5M, 35 mL) was dropped to the mixture slowly. The reaction mixture was stirred at room temperature for 3 hours. The mixture was poured into cold aqueous hydrochloric acid (10%, 60 mL). The mixture was extracted with ethyl acetate (200 mL) and the recovered top layer was filtered through a silica gel plug. The desired product 2-piperidino-3-methoxy-7,7-dimethyl-7H-benzo[C]fluoren-5-ol (10 g) was obtained by recrystallization from solution in ethyl acetate/hexanes.

Step 2

To a 500 mL one-neck flask was added 4-fluorobenzophenone (35 g), piperazine (13 g), potassium carbonate (22 g) and dimethyl sulfoxide (100 mL). The reaction mixture was heated to 100° C. for 20 hours. The mixture was cooled to room temperature and poured into water (400 mL). The mixture was extracted with chloroform (200 mL) and the recovered bottom layer was dried over sodium sulfate. The solvent was removed and the product was dried in vacuum oven at 60° C. for 6 hours to afford 40 g of waxy 4-piperazinobenzophenone. The product was used as is in next step without further purification.

Step 3

To a 500 mL beaker was added the waxy product from Step 3 (30 g) and anhydrous dimethylformamide (50 mL). Sodium acetylide xylene slurry (18 wt %, 90 g) was dropped to the mixture slowly. The reaction mixture was stirred with a glass stirring bar. The mixture was poured into water (400 mL). The mixture was extracted with ethyl acetate (200 mL) and the recovered top layer was filtered through a silica gel plug with ethyl acetate and methanol mixture as eluent. Solid product was obtained by recrystallization from the condensed major fraction. The solid 1-phenyl-1-(4-piperizinophenyl)-2-propyn-1-ol was filtered off and dried in a vacuum oven at 60° C. for 3 hours to afford 17 g of off-white solid.

Step 4

To a 500 mL one-neck flask was added the product from Step 3 (17 g), 4-hydroxy-5,6-di-t-butyltoluene (0.05 g) and anhydrous tetrahydrofuran (100 mL). 2-Isocyanatoethyl methacrylate (9 mL) was dropped to the mixture slowly. The reaction mixture was heated to reflux for 1 hour. The reaction mixture was condensed to lesser volume. The residue solution was filtered through a silica gel plug. The major product, 1-phenyl-1-(4-(4-(4-(2-(methacryloxy)ethoxy)-4-oxobutanoyl)piperazin-1-yl)phenyl)-2-propyn-1-ol, was obtained as an oily residue and used as is in next step without further purification.

Step 5

To a 250 mL one-neck flask was added the product from Step 1(10 g), pyridinium p-toluenesulfonate (0.7 g), trimethyl orthoformate (8 mL) and 1,2-dichloroethane (150 mL). The reaction mixture was heated to reflux. The product from Step 4 was added to the mixture in portions until no product from Step 2 was observed by TLC analysis. Heating was stopped and the reaction mixture was condensed to lesser volume and the residue was filtered through a silica gel plug. The major fraction was condensed to lesser volume. Solid product was obtained by recrystallization from solution in ethyl acetate/hexanes. Off-white solid (14 g) was filtered off. NMR analysis indicated the structure was consistent with 6-methoxy-7-(piperidin-1-yl)-13,13-dimethyl-3-phenyl-3-(4-(4-(4-(2-(methacryloxy)ethoxy)-4-oxobutanoyl)piperazin-1-yl)phenyl-3H,13H-indeno[2',3':3,4]naphtho[1,2-b]pyran as shown in the following graphic formula:

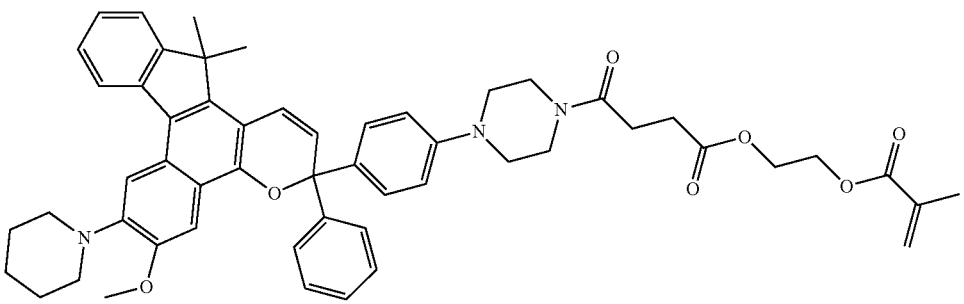 [SMILES: C=C(C)C(=O)OCCOC(=O)CCC(=O)N1CCN(c2ccc(C3(c4ccccc4)C=Cc4c5c(c6cc(N7CCCCC7)c(OC)cc6c4O3)-c3ccccc3C5(C)C)cc2)CC1]

Example 4

Step 1

To a 2 L three-neck flask was added 4-t-butylbenzoyl chloride (100 mL), veratrole (70 mL) and methylene chloride (800 mL). The flask was seated in ice bath. Anhydrous aluminum chloride (100 g) was added to the flask through a solid addition funnel slowly. The mixture was stirred at room temperature for 1 hour and then poured into ice water (1 L). Hydrochloric acid (12N, 150 mL) was added to the mixture. The bottom layer was isolated. The top layer was further extracted with methylene chloride twice (400+200 mL). The combined organic layers were washed with brine (200 mL) and filtered over magnesium sulfate. The final solution was condensed to an oily residue and the residue was dried in vacuum oven to provide 150 g waxy 3,4-dimethoxy-4'-t-butylbenzophenone.

Step 2

To a 2 L four-neck flask with overhead stirring was added the product from Step 1 (101 g), toluene (1.5 L) and potassium t-butoxide (50 g). Dimethyl succinate (60 mL) was added to the flask through addition funnel over 30 minutes. The reaction mixture was heated to 90° C. for 3 hours. The slurry was cooled and poured into ice water (1 L). The bottom water layer was acidified by hydrochloric acid (12N, 100 mL). The resulting slurry was extracted with ethyl acetate (1 L) and the top layer was washed with water and dried over sodium sulfate. The final solution was condensed to oily residue and the residue was dried in vacuum oven at 60° C. for 8 hours to afford 147 g of waxy solid, 4-(3,4-dimethoxyphenyl)-4-(4-t-butylphenyl)-3-methoxycarbonyl-3-butenoic acid. The product was used as is in next step without further purification.

Step 3

To a 1 L one-neck flask with water condenser was added the product from Step 2 (147 g) and acetic anhydride (300 mL). The mixture was heated to reflux for 5 hours and then condensed under reduced pressure and the oily product, 1-(4-t-butylphenyl)-2-methoxycarbonyl-4-acetoxy-6,7-dimethoxynaphthylene, was used as is in next step.

Step 4

To a 1 L one-neck flask with water condenser was added the product from Step 3 (160 g), hydrochloric acid (12N, 5 mL) and methanol (500 mL). The reaction mixture was heated to reflux for 3 hours and then condensed to an oily residue. The oily residue was dissolved in small amount of methylene chloride (100 mL) and the solution was filtered through a silica gel plug. Solid product was obtained by recrystallization from condensed major fraction. The 1-(4-t-butylphenyl)-2-methoxycarbonyl-4-hydroxy-6,7-dimethoxynaphthylene was dried in vacuum oven at 60° C. for 2 hours to afford off-white solid (65 g).

Step 5

To a 1 L one-neck flask was added the product from Step 4 (40 g) and anhydrous tetrahydrofuran (150 mL). The flask was seated in ice bath. Methyl magnesium chloride in tetrahydrofuran solution (3M, 150 mL) was dropped to the mixture slowly. Ice bath was removed upon the addition. The reaction mixture was stirred at room temperature for overnight. The mixture was poured into icy water (400 mL). The resulting slurry was acidified with hydrochloric acid (12N, 70 mL). The mixture was extracted with ethyl acetate (300 mL). The top layer was washed with water (600 mL) and brine (200 mL) and dried over sodium sulfate. The solution was filtered off and condensed to lesser volume. Solid 1-(4-t-butylphenyl)-2-(1-methyl-1-hydroxyethyl)-4-hydroxy-6,7-dimethoxynaphthylene was obtained by recrystallization from the condensed solution (30 g).

Step 6

To a 500 mL single neck flask equipped with Dean-Stark trap and water condenser was added the product from Step 5 (30 g), dodecyl benzene sulfonic acid (0.2 g) and xylene (150 mL). The mixture was heated to reflux for 3 hours. The mixture was cooled to room temperature. Solid product was recrystallized out from the reaction mixture. The 2,3-dimethoxy-7,7-dimethyl-9-(4-t-butylphenyl)-7H-benzo[C]fluoren-5-ol product was dried in vacuum oven at 80° C. for 4 hours to provide off-red solid (24 g).

Step 7

To a 500 mL one-neck flask was added the solid product from Step 6 (10 g), perhydroisoquinoline (7 mL) and anhydrous tetrahydrofuran (60 mL). n-Butyl lithium in hexane solution (2.5M, 29 mL) was dropped to the mixture slowly. The reaction mixture was stirred at room temperature for 20 hours. The mixture was poured into water (100 mL). The mixture was acidified with hydrochloric acid (10%, 20 mL) and then basified with sat'd sodium bicarbonate (100 mL). The mixture was extracted with ethyl acetate (200 mL). The top layer was washed with water (100 mL) and brine (100 mL) and dried over sodium sulfate. The solution was condensed to lesser volume. Solid 2-perhydroisoquinolin2(1H)- yl-3-methoxy-7,7-dimethyl-9-(4-t-butylphenyl)-7H-benzo[C]fluoren-5-ol was obtained by recrystallization from condensed solution (8 g).

Step 8

To a 1 L two-neck flask was added 4-fluorobenzophenone (100 g) and 2-methyl piperazine (60 g), triethyl amine (160 mL) and dimethyl sulfoxide (200 mL). The flask was seated in oil bath. The oil bath was heated to 100° C. for 24 hours. The mixture was cooled to room temperature and then poured into water (300 mL). The mixture was extracted with chloroform (300 mL). The bottom layer was separated and washed with water (500 mL) and brine (300 mL). The final solution was condensed and the residue was filtered off a silica gel plug. The major fraction was condensed to afford yellow oily 4-(3-methylpiperazino)benzophenone (130 g).

Step 9

To a 1 L two-neck flask equipped with overhead stirring was added the product from Step 8 (130 g) and anhydrous dimethylformamide (150 mL). The reaction flask was seated on ice bath. Sodium acetylide in xylene (22 wt %, 212 g) was added to the reaction flask through addition funnel. Ice bath was removed upon the addition. The reaction mixture was stirred at room temperature for 2 hours and then poured into ice water (500 mL). Solid product was filtered off. The filtrate was extracted with ethyl acetate (500 mL). The top layer was washed with water (800 mL) and brine (300 mL). The final solution was condensed to lesser volume. Solid product was obtained by recrystallization from condensed solution. The combined solid, 1-phenyl-1-(4-3-methylpiperazinophenyl)-2-propyn-1-ol was dried in vacuum oven to provide 70 g off-white solid.

Step 10

To a 1 L one-neck flask with water condenser was added 4-hydroxy-5,6-di-t-butyltoluene (0.05 g), 4-(2-(methacryloyloxy)ethoxy)-4-oxobutanoic acid (30 mL) and anhydrous tetrahydrofuran (250 mL). Carbonyldiimidazole (20 g) was added to the mixture. The mixture was stirred at room temperature for 1 hour. The product from Step 9 (31 g) in anhydrous tetrahydrofuran (100 mL) was added to the mixture through an addition funnel. The mixture was stirred at room temperature for 1 hour and then condensed to lesser volume. The oily residue was filtered through a silica gel plug. The major fraction was condensed to provide oily 1-phenyl-1-(4-(4-(4-(2-(methacryloxy)ethoxy)-4-oxobutanoyl)3-methylpiperazin-1-yl)phenyl)-2-propyn-1-ol, (30 g).

Step 11

To a 250 mL one-neck flask was added the product from Step 7 (7 g), pyridinium p-toluenesulfonic acid (0.5 g), trimethyl orthoformate (5 mL) and 1,2-dichloroethane (120 mL). The reaction mixture was heated to reflux. The product from Step 5 (7.5 g) was added to the mixture in portions. Heating was stopped and the reaction mixture was condensed and the residue was filtered through a silica gel plug. The major fraction was subjected to another silica gel column. The product was obtained as a purple foamy solid after dried in a vacuum oven (11 g). NMR indicated the structure was consistent with 6-methoxy-7-(octahydroisoquinolin-2(1H)-yl)-11-(tert-butyl)-13,13-dimethyl-3-phenyl-3-(4-(4-(4-(2-(methacryloxy)ethoxy)-4-oxobutanoyl)3-methylpiperazin-1-yl)phenyl-3H,13H-indeno[2',3':3,4]naphtho[1,2-b]pyran shown in the following graphic formula:

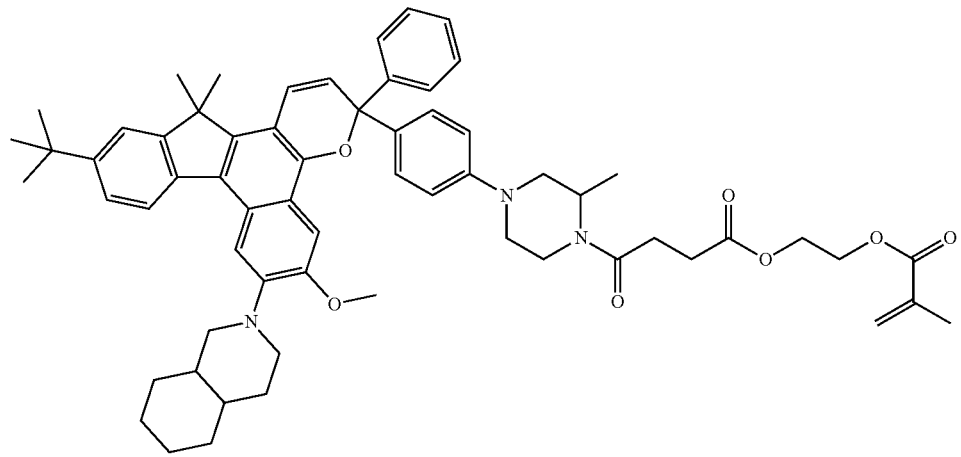 [SMILES: C=C(C)C(=O)OCCOC(=O)CCC(=O)N1CCN(c2ccc(C3(c4ccccc4)C=Cc4c5c(c6cc(N7CCC8CCCCC8C7)c(OC)cc6c4O3)-c3ccc(C(C)(C)C)cc3C5(C)C)cc2)CC1C]

Example 5

Step 1

The procedure of Step 2 of Example 1 was followed except dioctyl amine was used in place of piperazine to afford 2-dioctylamino-3-methoxy-7,7-dimethyl-9-(2-methoxyphenyl)-7H-benzo[C]fluoren-5-ol.

Step 2

To a 250 mL one-neck flask was added the product from Step 1 (7 g), pyridinium p-toluenesulfonate (2.6 g), trimethyl orthoformate (6 mL) and 1,2-dichloroethane (150 mL). The reaction mixture was heated to reflux. The product from Step 10 of Example 4 (7 g) was added to the mixture in portions. Heating was stopped after 4 hours and the reaction mixture was condensed to lesser volume and the residue was filtered through a silica gel plug. The major fraction was further purified by silica gel chromatography. The product was obtained as purple foamy solid after dried in vacuum oven (6 g). NMR analysis indicated the structure was consistent with 6-methoxy-7-(dioctylamino)-13,13-dimethyl-3-phenyl-3-(4-(4-(4-(2-(methacryloxy)ethoxy)-4-oxobutanoyl)-3-methylpiperazin-1-yl)phenyl-3H,13H-indeno[2',3':3,4]naphtho[1,2-b]pyran, shown in the following graphic formula:

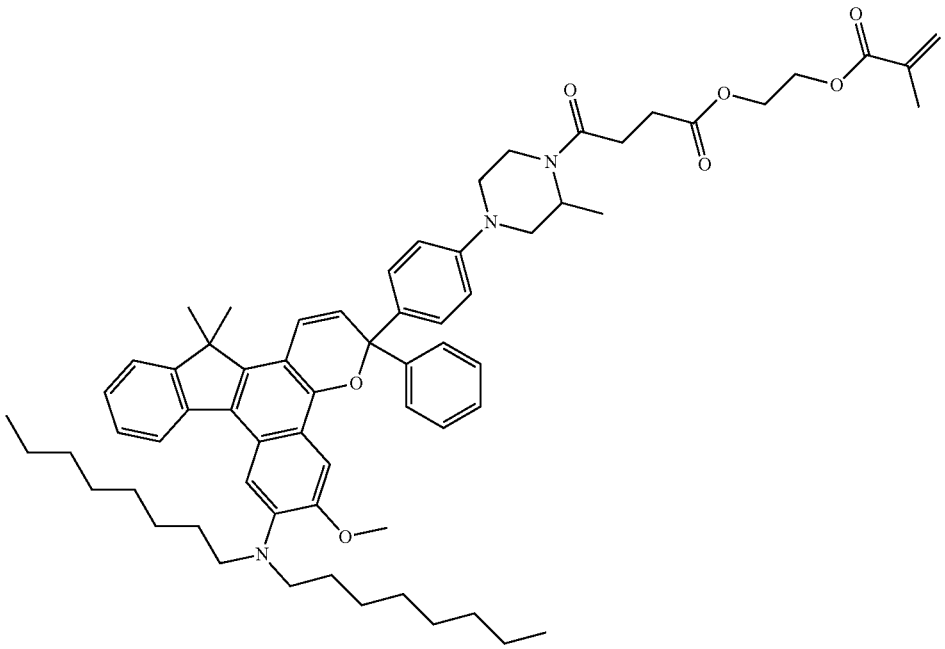 [SMILES: C=C(C)C(=O)OCCOC(=O)CCC(=O)N1CCN(c2ccc(C3(c4ccccc4)C=Cc4c5c(c6cc(N(CCCCCCCC)CCCCCCCC)c(OC)cc6c4O3)-c3ccccc3C5(C)C)cc2)CC1C]

Example 6

Step 1

The procedure of Step 7 of Example 4 was followed except piperazine was used in place of perhydroisoquinoline to provide 2-piperazino-3-methoxy-7,7-dimethyl-9-(4-t-butylphenyl)-7H-benzo[C]fluoren-5-ol.

Step 2

To a 250 mL one-neck flask was added the product from Step 1 (6 g), pyridinium p-toluenesulfonate (1 g), trimethyl orthoformate (5 mL) and 1,2-dichloroethane (100 mL). The reaction mixture was heated to reflux. The product from Step 4 of Example 3 (7 g) was added to the mixture in portions. Heating was stopped after 4 hours and the reaction mixture was condensed to lesser volume and the residue was filtered through a silica gel plug. The major fraction was further purified by silica gel chromatography. The product was obtained as purple foamy solid after dried in vacuum oven (6 g). NMR analysis indicated the structure was consistent with 6-methoxy-7-(piperidin-1-yl)-11-(tert-butyl)-13,13-dimethyl-3-phenyl-3-(4-(4-(4-(2-(methacryloxy)ethoxy)-4-oxobutanoyl)piperazin-1-yl)phenyl-3H,13H-indeno[2',3':3,4]naphtho[1,2-b]pyran, shown in the following graphic formula:

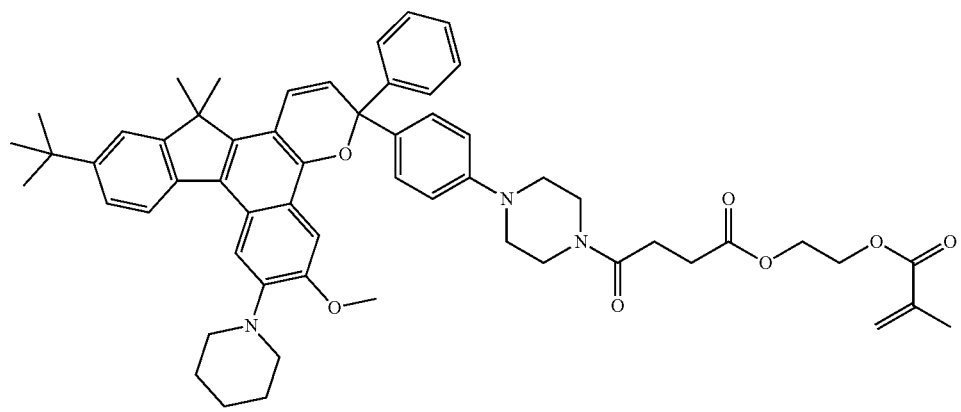 [SMILES: C=C(C)C(=O)OCCOC(=O)CCC(=O)N1CCN(c2ccc(C3(c4ccccc4)C=Cc4c5c(c6cc(N7CCCCC7)c(OC)cc6c4O3)-c3ccc(C(C)(C)C)cc3C5(C)C)cc2)CC1]

Example 7

Step 1

The procedure of Step 10 of Example 4 was followed except 6-acryamidohexanoic acid was used in place of 4-(2-(methacryloyloxy)ethoxy)-4-oxobutanoic acid to afford 1-phenyl-1-(4-(4-(6-acrylamidohexanoyl)-3-methylpiperazin-1-yl)phenyl)-2-propyn-1-ol.

Step 2

To a 250 mL one-neck flask was added the product from Step 7 of Example 4 (4 g), the product from Step 1 (4 g), dodecyl benzene sulfonic acid (0.6 g) and 1,2-dichloroethane (100 mL). The reaction mixture was heated to reflux for 8 hours and then condensed to lesser volume and the residue was filtered through a silica gel plug. The major fraction was further purified by silica gel chromatography. The product was obtained as purple foamy solid after dried in vacuum oven (3 g). NMR analysis indicated the structure was consistent with 6-methoxy-7-(octahydroisoquinolin-2(1H)-yl)-1'-(tert-butyl)-13,13-dimethyl-3-phenyl-3-(4-(4-(6-acrylamidohexanoyl)-3-methylpiperazin-1-yl)phenyl-3H,13H-indeno[2',3':3,4]naphtho[1,2-b]pyran, shown in the following graphic formula.

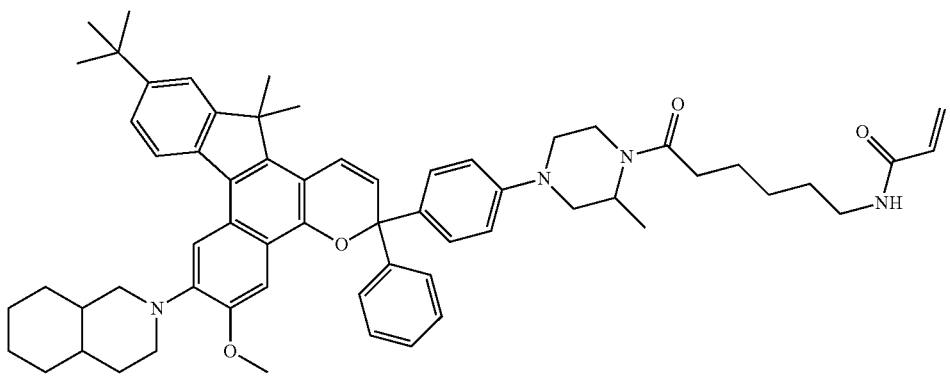 [SMILES: C=CC(=O)NCCCCCC(=O)N1CCN(c2ccc(C3(c4ccccc4)C=Cc4c5c(c6cc(N7CCC8CCCCC8C7)c(OC)cc6c4O3)-c3ccc(C(C)(C)C)cc3C5(C)C)cc2)CC1C]

Example 8

Step 1

To a 50 mL single-neck flask was added 4-(2-(methacryloyloxy)ethoxy)-4-oxobutanoic acid (5.4 mL), isophorone diisocyanate (10 g), dibutyltin dilaurate (0.01 g) and anhydrous tetrahydrofuran (50 mL). The mixture was heated to 55° C. for 2 hours and then cooled to room temperature. The solid product from Step 9 of Example 4 (14 g) was added to the mixture and the final mixture was stirred at room temperature for 10 minutes and then condensed to lesser volume and the residue was filtered through a silica gel plug. The major product was obtained as oily residue after silica gel chromatography. NMR analysis indicated the structure was consistent with 1-phenyl-1-(4-(4-(((5-(((2-(methacryloxy)ethoxy)carbonyl)amino)-1,3,3-trimethylcyclohexyl)methyl)carbamoyl)-3-methylpiperazin-1-yl)phenyl)-2-propyn-1-ol.

Step 2

To a 100 mL one-neck flask was added the product from Step 7 of Example 4 (0.9 g), the product from Step 1 (1.5 g), dodecyl benzene sulfonic acid (0.2 g) and 1,2-dichloroethane (20 mL). The reaction mixture was heated to reflux for 2 hours and then condensed to lesser volume. The residue was filtered through a silica gel plug. The major fraction was further purified by silica gel chromatography. The product was obtained as purple foamy solid after dried in vacuum oven (1.5 g). NMR analysis indicated the structure was consistent with 6-methoxy-7-(octahydroisoquinolin-2(1H)-yl)-11-(tert-butyl)-13,13-dimethyl-3-phenyl3-(4-(4-(((5-(((2-(methacryloxy)ethoxy)carbonyl)amino)-1,3,3-trimethylcyclohexyl)methyl)carbamoyl)-3-methylpiperazin-1-yl) phenyl-3H,13H-indeno[2',3':3,4]naphtho[1,2-b]pyran, shown in the following graphic formula:

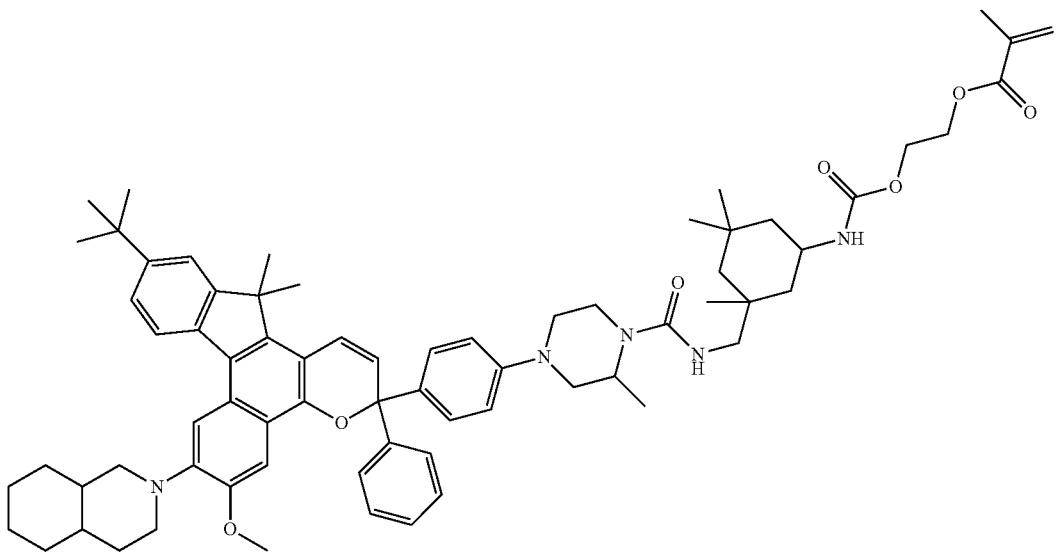 [SMILES: C=C(C)C(=O)OCCOC(=O)NC1CC(C)(C)CC(C)(CNC(=O)N2CCN(c3ccc(C4(c5ccccc5)C=Cc5c6c(c7cc(N8CCC9CCCCC9C8)c(OC)cc7c5O4)-c4ccc(C(C)(C)C)cc4C6(C)C)cc3)CC2C)C1]

Example 9

Step 1

The procedure of Step 7 of Example 4 was followed except piperidine was used in place of perhydroisoquinoline to afford 2-(piperidin-1-yl)-3-methoxy-7,7-dimethyl-9-(4-t-butylphenyl)-7H-benzo[C]fluoren-5-ol.

Step 2

To a 250 mL one-neck flask was added the product from Step 1 (6 g), pyridinium p-toluenesulfonate (1 g), trimethyl orthoformate (5 mL) and 1,2-dichloroethane (100 mL). The reaction mixture was heated to reflux. The product from Step 1 of Example 8 (5 g) was added to the mixture in portions. Heating was stopped after 8 hours and the reaction mixture was condensed to lesser volume and the residue was filtered through a silica gel plug. The major fraction was further purified by silica gel chromatography. The product was obtained as purple foamy solid after dried in vacuum oven (7 g). NMR analysis indicated the structure was consistent with 6-methoxy-7-(piperidin-1-yl)-11-(tert-butyl)-13,13-dimethyl-3-phenyl-3-(4-(4-(((5-(((2-(methacryloxy)ethoxy)carbonyl)amino)-1,3,3-trimethylcyclohexyl)methyl)carbamoyl)-3-methylpiperazin-1-yl)phenyl-3H,13H-indeno[2',3':3,4]naphtho[1,2-b]pyran, shown in the following graphic formula:

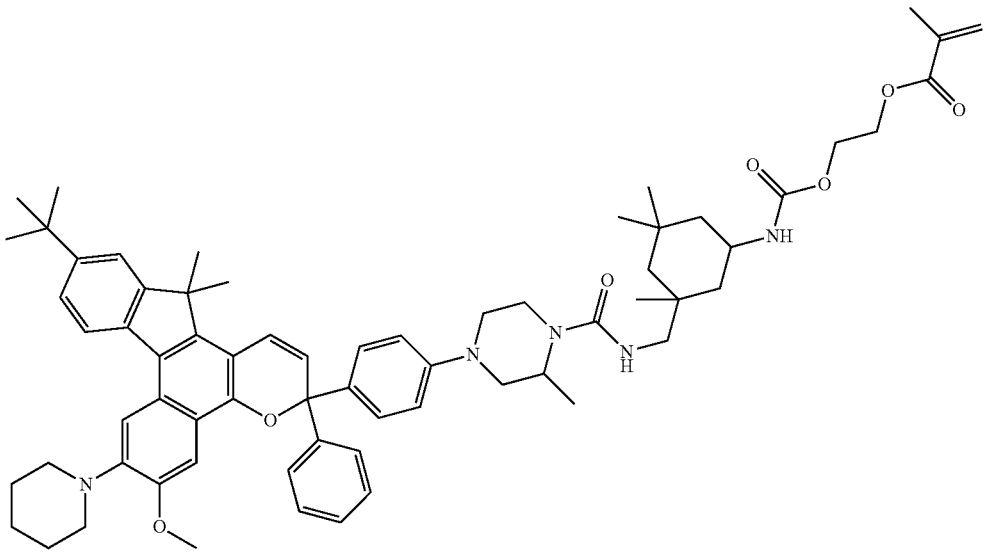 [SMILES: C=C(C)C(=O)OCCOC(=O)NC1CC(C)(C)CC(C)(CNC(=O)N2CCN(c3ccc(C4(c5ccccc5)C=Cc5c6c(c7cc(N8CCCCC8)c(OC)cc7c5O4)-c4ccc(C(C)(C)C)cc4C6(C)C)cc3)CC2C)C1]

Part 2

Photochromic Property Testing

Part 2A—Test Square Preparation

Testing was done with the compounds described in Examples 1-9 in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part polyethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on the optical bench, the photochromic test squares from Part 2A were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 98.6° F. (37° C.). The optical bench fitted with a Schott 3 mm KG-2 band-pass filter, neutral density filter(s) and a Newport Model #67005 300-watt Xenon arc lamp with Model #69911 power supply in association with a Newport Model 689456 Digital Exposure/Timer was used to control the intensity of the irradiance beam utilized for activation of the sample. A Uniblitz model #CS25S3ZMO with model #VMM-D3 controller) high-speed computer controlled shutter, a fused silica condensing lens for beam collimation of this activation lamp beam though a quartz glass water bath sample chamber.

A custom made broadband light source for monitoring response measurements was directed through the sample such that the angle between the activation source and the monitoring beam is 30 degrees with the sample positioned perpendicular to this monitoring beam. This broad beam light source is obtained by collecting and combining separately filtered light from a 100-Watt tungsten halogen lamp (controlled by a Lambda UP60-14 constant voltage powder supply) with a split-end, bifurcated fiber optical cable to enhance the short wavelength light intensity. After passing through the sample, this monitoring light was refocused into a 2-inch integrating sphere and fed to an Ocean Optics S2000 spectrophotometer by fiber optic cables. Ocean Optics Spectra-Suite and PPG proprietary software were used to measure response and control the operation of the optical bench.

The $\lambda_{max\text{-}vis}$ is the wavelength in the visible spectrum at which the maximum absorption of the activated-state form of the photochromic compound in a test square occurs. The $\lambda_{max\text{-}vis}$ wavelength was determined by testing the photochromic test squares in a Varian Cary 4000 UV-Visible spectrophotometer.

The change in Optical density at saturation for each test sample was determined by opening the shutter from the xenon lamp and measuring the transmittance after exposing the test chip to 1 W/m²UVA radiation for 30 minutes. The change in Optical density at saturation was calculated using the formula: $\Delta OD = \log(\% Tb / \% Ta)$, where % Tb is the percent transmittance in the bleached state, % Ta is the percent transmittance in the activated state both at the $\lambda_{max\text{-}vis}$ and the logarithm is to the base 10. The fade half life ("$T_{1/2}$") or bleach rate is the time interval in seconds for the absorbance of the activated-state form of the photochromic material in the test squares to reach one half the ΔOD at saturation value at 37° C., after removal of the source of activating light. The Sensitivity (ΔOD/Min) is a measure of how quickly the sample darkens and is calculated from the equation $\Delta OD_{sen} = \Delta OD_{5min} \times 12$.

The compounds of Examples 1, 2, 4 and 7 exhibited dual peak absorptions in the visible spectrum (lambda max visible) in distinct color regions. For each lambda max visible, the corresponding optical density (Δ OD/Min, and Δ OD at saturation) as well as fade half life are tabulated in Table 1 for the two bands (A and B) of peak absorption. The results are listed in Table 1 as follows.

TABLE 1

Photochromic Performance Results

| Example # | $\lambda_{max\text{-}vis}$ (nm) | Sensitivity (ΔOD/Min) | ΔOD at saturation | T ½ (sec) |
|---|---|---|---|---|
| 1A | 507 | 0.25 | 0.73 | 291 |
| 1B | 593 | 0.16 | 0.47 | 299 |
| 2A | 503 | 0.26 | 0.71 | 270 |
| 2B | 595 | 0.16 | 0.46 | 265 |
| 3 | 503 | 0.22 | 0.65 | 273 |
| 4A | 506 | 0.23 | 0.75 | 295 |
| 4B | 590 | 0.14 | 0.47 | 289 |
| 5 | 519 | 0.36 | 1.00 | 239 |
| 6 | 502 | 0.28 | 0.79 | 267 |
| 7 | 507 | 0.26 | 0.76 | 245 |
| 8 | 507 | 0.24 | 0.72 | 254 |
| 9A | 505 | 0.23 | 0.69 | 241 |
| 9B | 581 | 0.14 | 0.44 | 240 |

The present invention has been described with reference to specific details of particular embodiments thereof. It is not intended that such details be regarded as limitations upon the scope of the invention except insofar as and to the extent that they are included in the accompanying claims.

What is claimed is:

1. An indeno-fused naphthopyran represented by the following Formula (I),

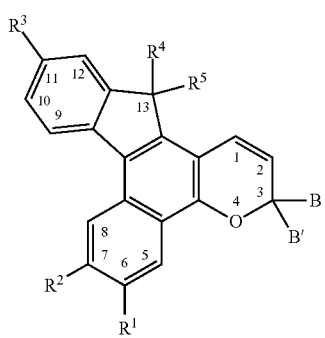

(I)

wherein,
$R^1$ is $R_6O$—, wherein $R_6$ is linear or branched $C_1$-$C_{20}$ alkyl, $C_3$-$C_{12}$ cycloalkyl, or $C_3$-$C_{12}$ heterocycloalkyl,
$R^2$ is
—$N(R_{11}')R_{12}'$, wherein $R_{11}'$ and $R_{12}'$ are each independently hydrogen, $C_1$-$C_8$ alkyl, $C_3$-$C_{20}$ cycloalkyl, or $C_1$-$C_{20}$ alkoxyalkyl, or $R_{11}'$ and $R_{12}'$ come together with the nitrogen atom to form a bridged ring $C_4$-$C_{20}$ hetero-bicycloalkyl, and a fused ring $C_3$-$C_{20}$ hetero-polycyclic alkyl, or
a nitrogen containing ring substituent represented by the following Formula (IIIA):

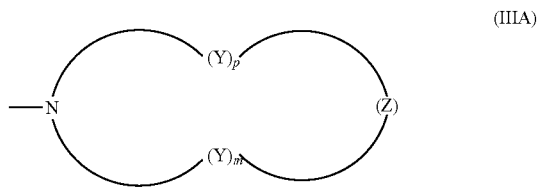

(IIIA)

wherein each —Y— is independently chosen for each occurrence from —$CH_2$—, —$CH(R_{13}')$—, —$C(R_{13}')_2$—, and Z is —Y—, —O—, —S—, —S(O)—, —$SO_2$—, —NH—, —$N(R_{13}')$—, wherein each $R_{13}'$ is independently $C_1$-$C_6$ alkyl, m is an integer 1, 2 or 3, and p is an integer 0, 1, 2, or 3, provided that when p is 0, Z is —Y—,
$R^3$ is linear or branched $C_1$-$C_{20}$ alkyl,
$R^4$ and $R^5$ are each independently linear or branched $C_1$-$C_{20}$ alkyl, $C_3$-$C_{12}$ cycloalkyl, or $R^4$ and $R^5$ together form an optionally substituted spirocycloalkyl group having from 3 to 10 carbon atoms in the spirocycloalkyl group inclusive of the spirocenter, the optional substituents of the spirocycloalkyl group being linear or branched $C_1$-$C_{20}$ alkyl, and
B and B' are each independently,
an aryl group that is mono-substituted with a reactive substituent or a compatiblizing substituent; an unsubstituted aryl group; a mono-, di-, tri- or tetra-substituted aryl group;
wherein the aryl substituents are each independently, hydroxy, halo, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, linear or branched $C_1$-$C_{12}$ alkyl, linear or branched $C_1$-$C_{12}$ haloalkyl, linear or branched $C_1$-$C_{12}$ alkoxy, mono($C_1$-$C_{12}$)alkoxy ($C_1$-$C_{12}$) alkyl, acryloxy, methacryloxy, halogen, or —C(=O)$R^{21}$ wherein $R^{21}$ is —$OR^{22}$, —$N(R^{23})R^{24}$, wherein $R^{22}$ is allyl, $C_1$-$C_6$ alkyl, $C_1$-$C_6$ alkoxy $C_2$-$C_4$)alkyl or $C_1$-$C_6$ haloalkyl, and $R^{23}$ and $R^{24}$ are each independently $C_1$-$C_6$ alkyl, $C_5$-$C_7$ cycloalkyl; or
an unsubstituted or mono-substituted group selected from the group consisting of pyrazolyl, imidazolyl, pyrazolinyl, imidazolinyl, pyrrolinyl, phenothiazinyl, phenoxazinyl, phenazinyl and acridinyl, said substituents being $C_1$-$C_{12}$ alkyl, $C_1$-$C_{12}$ alkoxy; or
a mono-substituted phenyl, said mono-substituted phenyl having a substituent located at the para position, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_t$— or [O—($CH_2$)$_t$]$_k$—, wherein t ranges from 2 to 6 and k ranges from 1 to 50, and wherein the substituent is connected to an aryl group on another photochromic material,
provided that $R^4$ and $R^5$ each are not hydroxyl or $R_7O$—, where $R_7$ is optionally substituted alkyl, optionally substituted cycloalkyl, optionally substituted heterocycloalkyl, optionally substituted aryl, or optionally substituted heteroaryl, and provided that one of B and B' is represented by the following Formula (VIIIb),

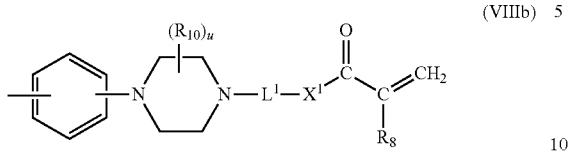

wherein $R_8$ is hydrogen or linear or branched $C_1$-$C_6$ alkyl, $X^1$ is O or NH, and $L^1$ is a divalent hydrocarbyl group optionally interrupted with at least one of —C(O)—, —C(O)O—, —C(O)NH—, —NH—, —O—, and combinations of two or more thereof, u is 0 to 4, and $R_{10}$ independently for each u is linear or branched $C_1$-$C_{10}$ alkyl or $C_3$-$C_{12}$ cycloalkyl.

2. The indeno-fused naphthopyran of claim 1, wherein, $R^1$ is $R_6$O—, wherein $R_6$ is linear or branched $C_1$-$C_6$ alkyl, $R^2$ is
—N($R_{11}'$)$R_{12}'$, wherein $R_{11}'$ and $R_{12}'$ are each independently hydrogen, $C_1$-$C_8$ alkyl, or $R_{11}'$ and $R_{12}'$ come together with the nitrogen atom to form fused ring $C_5$-$C_{15}$ hetero-polycyclic alkyl, or
said nitrogen containing ring substituent represented by Formula (IIIA),
$R^3$ is linear or branched $C_1$-$C_{15}$ alkyl,
$R^4$ and $R^5$ are each independently linear or branched $C_1$-$C_{20}$ alkyl, and
B and B' are each independently,
optionally substituted phenyl, the optional substituents of the optionally substituted phenyl being selected from the group consisting of fluoro, linear or branched $C_1$-$C_{12}$ alkyl, linear or branched $C_1$-$C_{12}$ haloalkyl, linear or branched $C_1$-$C_{12}$ alkoxy, optionally substituted piperidino, optionally substituted morpholino, and optionally substituted piperazino, the optional substituents of the piperidino, morpholino and piperazino substituents each being independently selected from the group consisting of linear or branched $C_1$-$C_{12}$ alkyl, linear or branched $C_1$-$C_{12}$ haloalkyl, and linear or branched $C_1$-$C_{12}$ alkoxy,
provided that one of B and B' is represented by Formula (VIIIb).

3. The indeno-fused naphthopyran of claim 1, wherein, $R^1$ is $R_6$O—, wherein $R_6$ is linear or branched $C_1$-$C_4$ alkyl, $R^2$ is
N($R_{11}'$)$R_{12}'$, wherein $R_{11}'$ and $R_{12}'$ are each independently hydrogen or $C_1$-$C_8$ alkyl,
N($R_{11}'$)$R_{12}'$ wherein $R_{11}'$ and $R_{12}'$ come together with the nitrogen atom to form optionally substituted piperidino, optionally substituted octahydroisoquinoline or optionally substituted decahydroisoquinoline, or optionally substituted morpholino,
the optional substituents of the piperidino, octahydroisoquinoline, decahydroisoquinoline, and morpholino groups each being independently selected from the group consisting of linear or branched $C_1$-$C_{12}$ alkyl, linear or branched $C_1$-$C_{12}$ haloalkyl, and linear or branched $C_1$-$C_{12}$ alkoxy,
$R^3$ is linear or branched $C_1$-$C_{10}$ alkyl,
$R^4$ and $R^5$ are each independently linear or branched $C_1$-$C_{10}$ alkyl, and
B and B' are each independently,
optionally substituted phenyl, the optional substituents being selected from the group consisting of fluoro, $C_1$-$C_6$ alkyl, $C_1$-$C_6$ alkoxy, optionally substituted piperidino, optionally substituted piperazino and optionally substituted morpholino, the optional substituents of the piperidino, piperazino and morpholino substituents each being independently selected from the group consisting of linear or branched $C_1$-$C_6$ alkyl, linear or branched $C_1$-$C_6$ haloalkyl, and linear or branched $C_1$-$C_6$ alkoxy,
provided that one of B and B' is represented by Formula (VIIIb).

4. The indeno-fused naphthopyran of claim 1, wherein $L^1$ is a divalent linking group represented by one of the following formulas,

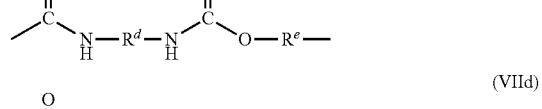

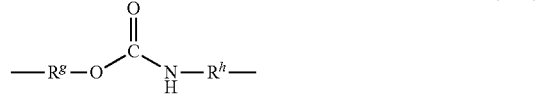

wherein $R^a$, $R^b$, $R^c$, $R^d$, $R^e$, $R^f$, $R^g$, and $R^h$ are each independently divalent optionally substituted linear or branched $C_1$-$C_{10}$ alkyl, or divalent optionally substituted $C_3$-$C_{12}$ cycloalkyl.

5. The indeno-fused naphthopyran of claim 1, wherein,
for Formula (VIIIb) $L^1$ is a divalent linking group represented by one of the following Formulas (VIIa) through (VIId),

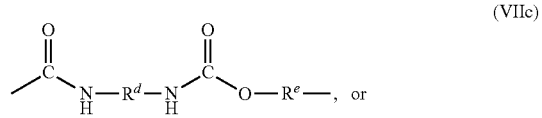

-continued (VIId)

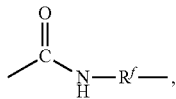

wherein $R^a$, $R^b$, $R^c$, $R^d$, $R^e$, and $R^f$ are each independently divalent optionally substituted linear or branched $C_1$-$C_{10}$ alkyl, or divalent optionally substituted $C_3$-$C_{12}$ cycloalkyl, and $R_{10}$ independently for each u is linear or branched $C_1$-$C_{10}$ alkyl.

6. The indeno-fused naphthopyran of claim 5, wherein, $R_{10}$ independently for each u is linear or branched $C_1$-$C_6$ alkyl.

7. The indeno-fused naphthopyran of claim 1, wherein said indeno-fused naphthopyran selected from the group consisting of:
   (c) 6-methoxy-7-(octahydroisoquinolin-2(1H)-yl)-11-(tert-butyl)-13,13 dimethyl-3-phenyl-3-(4-(4-(6-acrylamidohexanoyl)-3-methylpiperazin-1-yl)phenyl-3H, 13H-indeno[2',3':3,4]naphtho[1,2-b]pyran,
   (d) 6-methoxy-7-(octahydroisoquinolin-2(1H)-yl)-11-(tert-butyl)-13,13-dimethyl-3-phenyl-3-(4-(4-(((5-(((2-(methacryloxy)ethyl)carbamoyl)-1,3,3-trimethylcyclohexyl)methyl)carbamyl)-3-methylpiperazin-1-yl)phenyl-3H,13H-indeno[2',3':3,4]naphtho[1,2-b]pyran,
   (e) 6-methoxy-7-(piperidin-1-yl)-11-(tert-butyl)-13,13-dimethyl-3-phenyl-3-(4-(4-(((5-(((2-(methacryloxy)ethyl)carbamoyl)-1,3,3-trimethylcyclohexyl)methyl)carbamyl)-3-methylpiperazin-1-yl)phenyl -3H,13H-indeno[2',3':3,4]naphtho[1,2-b]pyran,
   (f) 6-methoxy-7-(octahydroisoquinolin-2(1H)-yl)-11-(tert-butyl)-13,13-dimethyl-3-phenyl-3-(4-(4-(4-(2-(methacryloxy)ethoxy)-4-oxobutanoyl)3-methylpiperazin-1-yl)phenyl-3H,13H-indeno[2',3':3,4]naphtho[1,2-b]pyran, and
   (g) 6-methoxy-7-(piperidin-1-yl)-11-(tert-butyl)-13,13-dimethyl-3-phenyl-3 (4-(4-(4-(2-(methacryloxy)ethoxy)-4-oxobutanoyl)piperazin-1-yl)phenyl-3H, 13H-indeno[2',3':3,4]naphtho[1,2-b]pyran.

8. A photochromic article comprising at least one indeno-fused naphthopyran according to claim 1.

9. The photochromic article of claim 8, wherein said photochromic article is selected from the group consisting of ophthalmic articles, display articles, windows, mirrors, active liquid crystal cell articles, and passive liquid crystal cell articles.

10. The photochromic article of claim 9, wherein said photochromic article is an ophthalmic article, said ophthalmic article being selected from the group consisting of corrective lenses, non-corrective lenses, contact lenses, intraocular lenses, magnifying lenses, protective lenses, and visors.

11. The photochromic article of claim 9, wherein said photochromic article is a display article, said display article being selected from the group consisting of screens, monitors, and security elements.

12. A photochromic composition comprising at least one indeno-fused naphthopyran according to claim 1 incorporated into at least a portion of an organic material, wherein said organic material is a polymeric material, an oligomeric material, a monomeric material, a mixture of two or more thereof, or a combination of two or more thereof.

13. The photochromic composition of claim 12, wherein the organic material is a polymeric material, said polymeric material being a poly(carbonate); a copolymer of ethylene and vinyl acetate; a copolymer of ethylene and vinyl alcohol; a copolymer of ethylene, vinyl acetate and vinyl alcohol; cellulose acetate butyrate; poly(urethane); poly(acrylate); poly(methacrylate); epoxy; an aminoplast functional polymer; poly(anhydride); poly(urea urethane); a N-alkoxymethyl(meth)acrylamide functional polymer; poly(siloxane); poly(silane); a mixture of two or more thereof; or a combination of two or more thereof.

14. The photochromic composition of claim 12, wherein the photochromic composition further comprises at least one of, a complementary photochromic material, a photoinitiator, a thermal initiator, a polymerization inhibitor, a solvent, a light stabilizer, a heat stabilizer, a mold release agent, a rheology control agent, a leveling agent, a free radical scavenger, and an adhesion promoter.

15. The photochromic composition of claim 12, wherein the photochromic composition is a coating composition.

* * * * *